US007910693B2

(12) United States Patent
Cuello et al.

(10) Patent No.: US 7,910,693 B2
(45) Date of Patent: Mar. 22, 2011

(54) PROSTATE CANCER DIAGNOSIS AND TREATMENT

(75) Inventors: Claudio Cuello, Westmount (CA); Uri Saragovi, Montréal (CA); Pierre Du Ruisseau, Laval (CA); Phil Gold, Westmount (CA); Serge Moffett, Montréal (CA)

(73) Assignee: ProScan Rx Pharma Inc., Montréal (CA)

( * ) Notice: Subject to any disclaimer, the term of this patent is extended or adjusted under 35 U.S.C. 154(b) by 779 days.

(21) Appl. No.: 11/568,089

(22) PCT Filed: Apr. 19, 2005

(86) PCT No.: PCT/CA2005/000601
§ 371 (c)(1),
(2), (4) Date: Oct. 1, 2007

(87) PCT Pub. No.: WO2005/100404
PCT Pub. Date: Oct. 27, 2005

(65) Prior Publication Data
US 2009/0131277 A1    May 21, 2009

Related U.S. Application Data

(60) Provisional application No. 60/562,991, filed on Apr. 19, 2004.

(51) Int. Cl.
*A61K 38/12*    (2006.01)
(52) U.S. Cl. ............ 530/317; 530/300; 530/328; 514/2; 514/9; 514/11; 514/15
(58) Field of Classification Search .................. 530/300, 530/317, 328, 350; 514/2, 9, 11, 15
See application file for complete search history.

(56) References Cited

U.S. PATENT DOCUMENTS

| 5,162,504 | A | 11/1992 | Horoszewicz |
| 6,107,090 | A | 8/2000 | Bander |
| 6,150,508 | A | 11/2000 | Murphy et al. |
| 6,830,894 | B1 * | 12/2004 | Blaschuk et al. ............ 435/7.21 |
| 2004/0033229 | A1 | 2/2004 | Maddon et al. |

FOREIGN PATENT DOCUMENTS

| EP | 05735593 | 7/2008 |
| WO | WO-2004067570 A2 | 8/2004 |
| WO | WO-2005100404 | 10/2005 |
| WO | WO-2006028429 A2 | 3/2006 |

OTHER PUBLICATIONS

Moffett et al. (Hybridoma (Larchmt). Dec. 2007; 26 (6): 363-72).*
Skolnick et al. (Trends in Biotechnology 2000; 18: 34-39).*
Bowie et al. (Science 1990; 257: 1306-1310).*
Burgess et al. (Journal of Cell Biology 1990; 111: 2129-2138).*
Lazar et al. (Molecular and Cellular Biology, 1988, 8: 1247-1252).*
Takada et al. (Mol. Endocrinol. 2000; 14 (5): 733-740).*
Guo et al. (Proc. Natl. Acad. Sci. USA. Jun. 22, 2004; 101 (25): 9205-9210).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Berezov et al. (J Med Chem. Aug. 2, 2001; 44 (16): 2565-74).*
Feng et al. (Immunol Lett. May 15, 2005; 98 (2): 311-6).*
Monfardini et al. (Proc Assoc Am Physicians. Nov. 1996; 108 (6): 420-31).*
Taub et al. (J Biol Chem. Mar. 25, 1992; 267 (9): 5977-84).*
Park et al. (Nat Biotechnol. Feb. 2000; 18 (2): 194-8).*
Casset et al. (Biochem Biophys Res Commun. Jul. 18, 2003; 307 (1): 198-205).*
Monnet et al. (J Biol Chem. Feb. 5, 1999; 274 (6): 3789-96).*
Ma, Q. et al., Anti-Prostate Specific Membrane Antigen Designer T Cells for Prostate Cancer Therapy, The Prostate (published online), 2004, 12-25, vol. 61:12.
Lupold, S.E. et al., Identification and Characterization of Nuclease-stabilized RNA Molecules That Bind Human Prostate Cancer Cells via the Prostate-specific Membrane Antigen, Cancer Research, 2002, 4029-4033, vol. 62:14.
Pirtskhalaishvili G et al Cancer Practice 2001 9(6) :295-306.
Horoszewicz et al. Can Res 1983 43 : 1809-1818.
Israeli et al. Can Res 1993 53 :227-230.
Horoszewicz et al. Anticancer Res 1987 7 :927-935.
Bander Sem in Oncology 1994 21(5):607-612.
Williams et al. JBC 1991 266:5182.
Habeeb AF Anal. Biochem 1973 56, 60-65.
Rich RL and Myszka DG Curr. Opin. Biotechnol. 2000 11, 54-61.
Limbird LE, Cell Surface Receptors, A short Course on Theory and Methods, 3rd edition, 2005 Springer NY USA, Cover and Table of Contents only.
Lupold Shawn E et al. Proceedings of the American Association for Cancer Research Annual Meeting 2003 (44) 148.
Lupold Shawn E et al. Proceedings of the American Association for Cancer Research Annual Meeting 2004 (45) 868.
Lupold Shawn E et al. Molecular Cancer Therapeutics 2004 (3) 597-603.
McConnell S J et al. Molecular Diversity, Escom Science Publishers 1996 165-176.
Zhu Z Yet al. Cell Research 1999 (9) 271-280.
Warren P et al. Cancer Research, American Association for Cancer Research 2001 (61) 6783-6787.
Aggarwal Saurabh et al. Cancer Research 2006 (66) 9171-9177.

* cited by examiner

*Primary Examiner* — Stephen L Rawlings
(74) *Attorney, Agent, or Firm* — Janique Forget; Fasken Martineau DuMoulin LLP

(57) ABSTRACT

The present invention relates to novel mimetopes of anti-PSMA antibodies and their use for detecting, imaging, staging, treating and monitoring of prostate cancer, and/or metastatis thereof. The present invention also relates to novel pharmaceutical compositions for the treatment of prostate cancer. Furthermore the present invention relates to assay systems and kits for detecting, imaging, staging, treating and monitoring of prostate cancer, and/or metastasis thereof.

8 Claims, 9 Drawing Sheets

```
ATGTGGAATCTCCTTCACGAAACCGACTCGGCTGTGGCCACCGCGCGCCGCCCGC
GCTGGCTGTGCGCTGGGGCGCTGGTGCTGGCGGGTGGCTTCTTTCTCCTCGGCTTC
CTCTTCGGGTGGTTTATAAAATCCTCCAATGAAGCTACTAACATTACTCCAAAGC
ATAATATGAAAGCATTTTTGGATGAATTGAAAGCTGAGAACATCAAGAAGTTCTT
ATATAATTTTACACAGATACCACATTTAGCAGGAACAGAACAAAACTTTCAGCTT
GCAAAGCAAATTCAATCCCAGTGGAAAGAATTTGGCCTGGATTCTGTTGAGCTAG
CACATTATGATGTCCTGTTGTCCTACCCAAATAAGACTCATCCCAACTACATCTCA
ATAATTAATGAAGATGGAAATGAGATTTTCAACACATCATTATTTGAACCACCTC
CTCCAGGATATGAAAATGTTTCGGATATTGTACCACCTTTCAGTGCTTTCTCTCCT
CAAGGAATGCCAGAGGGCGATCTAGTGTATGTTAACTATGCACGAACTGAAGAC
TTCTTTAAATTGGAACGGGACATGAAAATCAATTGCTCTGGGAAAATTGTAATTG
CCAGATATGGGAAAGTTTTCAGAGGAAATAAGGTTAAAAATGCCCAGCTGGCAG
GGGCCAAAGGAGTCATTCTCTACTCCGACCCTGCTGACTACTTTGCTCCTGGGGT
GAAGTCCTATCCAGATGGTTGGAATCTTCCTGGAGGTGGTGTCCAGCGTGGAAAT
ATCCTAAATCTGAATGGTGCAGGAGACCCTCTCACACCAGGTTACCCAGCAAATG
AATATGCTTATAGGCGTGGAATTGCAGAGGCTGTTGGTCTTCCAAGTATTCCTGTT
CATCCAATTGGATACTATGATGCACAGAAGCTCCTAGAAAAAATGGGTGGCTCAG
CACCACCAGATAGCAGCTGGAGAGGAAGTCTCAAAGTGCCCTACAATGTTGGAC
CTGGCTTTACTGGAAACTTTTCTACACAAAAAGTCAAGATGCACATCCACTCTAC
CAATGAAGTGACAAGAATTTACAATGTGATAGGTACTCTCAGAGGAGCAGTGGA
ACCAGACAGATATGTCATTCTGGGAGGTCACCGGGACTCATGGGTGTTTGGTGGT
ATTGACCCTCAGAGTGGAGCAGCTGTTGTTCATGAAATTGTGAGGAGCTTTGGAA
CACTGAAAAAGGAAGGGTGGAGACCTAGAAGAACAATTTTGTTTGCAAGCTGGG
ATGCAGAAGAATTTGGTCTTCTTGGTTCTACTGAGTGGGCAGAGGAGAATTCAAG
ACTCCTTCAAGAGCGTGGCGTGGCTTATATTAATGCTGACTCATCTATAGAAGGA
AACTACACTCTGAGAGTTGATTGTACACCGCTGATGTACAGCTTGGTACACAACC
TAACAAAAGAGCTGAAAAGCCCTGATGAAGGCTTTGAAGGCAAATCTCTTTATGA
AGTTGGACTAAAAAAAGTCCTTCCCCAGAGTTCAGTGGCATGCCCAGGATAAGC
AAATTGGGATCTGGAAATGATTTTGAGGTGTTCTTCCAACGACTTGGAATTGCTTC
AGGCAGAGCACGGTATACTAAAAATTGGGAAACAAACAAATTCAGCGGCTATCC
ACTGTATCACAGTGTCTATGAAACATATGAGTTGGTGGAAAAGTTTTATGATCCA
ATGTTTAAATATCACCTCACTGTGGCCCAGGTTCGAGGAGGGATGGTGTTTGAGC
TAGCCAATTCCATAGTGCTCCCTTTTGATTGTCGAGATTATGCTGTAGTTTTAAGA
AAGTATGCTGACAAAATCTACAGTATTTCTATGAAACATCCACAGGAAATGAAGA
CATACAGTGTATCATTTGATTCACTTTTTTCTGCAGTAAAGAATTTTACAGAAATT
GCTTCCAAGTTCAGTGAGAGACTCCAGGACTTTGACAAAAGCAACCCAATAGTAT
TAAGAATGATGAATGATCAACTCATGTTTCTGGAAAGAGCATTTATTGATCCATT
AGGGTTACCAGACAGGCCTTTTTATAGGCATGTCATCTATGCTCCAAGCAGCCAC
AACAAGTATGCAGGGGAGTCATTCCCAGGAATTTATGATGCTCTGTTTGATATTG
AAAGCAAAGTGGACCCTTCCAAGGCCTGGGGAGAAGTGAAGAGACAGATTTATG
TTGCAGCCTTCACAGTGCAGGCAGCTGCAGAGACTTTGAGTGAAGTAGCCTAA
```

FIG.1

MWNLLHETDSAVATARRPRWLCAGALVLAGGFFLLGFLFGWFIKSSNEATNITPKHN
MKAFLDELKAENIKKFLYNFTQIPHLAGTEQNFQLAKQIQSQWKEFGLDSVELAHYD
VLLSYPNKTHPNYISIINEDGNEIFNTSLFEPPPPGYENVSDIVPPFSAFSPQGMPEGDLV
YVNYARTEDFFKLERDMKINCSGKIVIARYGKVFRGNKVKNAQLAGAKGVILYSDP
ADYFAPGVKSYPDGWNLPGGGVQRGNILNLNGAGDPLTPGYPANEYAYRRGIAEAV
GLPSIPVHPIGYYDAQKLLEKMGGSAPPDSSWRGSLKVPYNVGPGFTGNFSTQKVKM
HIHSTNEVTRIYNVIGTLRGAVEPDRYVILGGHRDSWVFGGIDPQSGAAVVHEIVRSF
GTLKKEGWRPRRTILFASWDAEEFGLLGSTEWAEENSRLLQERGVAYINADSSIEGN
YTLRVDCTPLMYSLVHNLTKELKSPDEGFEGKSLYESWTKKSPSPEFSGMPRISKLGS
GNDFEVFFQRLGIASGRARYTKNWETNKFSGYPLYHSVYETYELVEKFYDPMFKYH
LTVAQVRGGMVFELANSIVLPFDCRDYAVVLRKYADKIYSISMKHPQEMKTYSVSFD
SLFSAVKNFTEIASKFSERLQDFDKSNPIVLRMMNDQLMFLERAFIDPLGLPDRPFYRH
VIYAPSSHNKYAGESFPGIYDALFDIESKVDPSKAWGEVKRQIYVAAFTVQAAAETLS
EVA

FIG.2

SEQUENCE LISTING

<160> NUMBER OF SEQ ID NOS: 43

<210> SEQ ID NO 1
<211> LENGTH: 2253
<212> TYPE: DNA
<213> ORGANISM: Homo sapiens

<400> SEQUENCE: 1

```
atgtggaatc tccttcacga aaccgactcg gctgtggcca ccgcgcgccg cccgcgctgg      60
ctgtgcgctg gggcgctggt gctggcgggt ggcttctttc tcctcggctt cctcttcggg     120
tggtttataa aatcctccaa tgaagctact aacattactc aaagcataa tatgaaagca      180 tttttggatg aattgaaagc tgagaacatc aagaagttct tatataattt tacacagata     240
ccacatttag caggaacaga acaaaacttt cagcttgcaa agcaaattca atcccagtgg     300
aaagaatttg gcctggattc tgttgagcta gcacattatg atgtcctgtt gtcctaccca     360
aataagactc atcccaacta catctcaata attaatgaag atggaaatga gattttcaac     420
acatcattat ttgaaccacc tcctccagga tatgaaaatg tttcggatat tgtaccacct     480
ttcagtgctt tctctcctca aggaatgcca gagggcgatc tagtgtatgt taactatgca     540
cgaactgaag acttctttaa attggaacgg gacatgaaaa tcaattgctc tgggaaaatt     600
gtaattgcca gatatgggaa agttttcaga ggaaataagg ttaaaaatgc ccagctggca     660
ggggccaaag gagtcattct ctactccgac cctgctgact actttgctcc tggggtgaag     720
tcctatccag atggttggaa tcttcctgga ggtggtgtcc agcgtggaaa tatcctaaat     780
```

```
ctgaatggtg caggagaccc tctcacacca ggttacccag caaatgaata tgcttatagg    840
cgtggaattg cagaggctgt tggtcttcca agtattcctg ttcatccaat tggatactat    900
gatgcacaga agctcctaga aaaaatgggt ggctcagcac caccagatag cagctggaga    960
ggaagtctca aagtgcccta caatgttgga cctggcttta ctggaaactt ttctacacaa   1020
aaagtcaaga tgcacatcca ctctaccaat gaagtgacaa gaatttacaa tgtgataggt   1080
actctcagag gagcagtgga accagacaga tatgtcattc tggaggtca ccggactca    1140
tgggtgtttg gtggtattga ccctcagagt ggagcagctg ttgttcatga aattgtgagg   1200
agctttggaa cactgaaaaa ggaagggtgg agacctagaa gaacaatttt gtttgcaagc   1260
tgggatgcag aagaatttgg tcttcttggt tctactgagt gggcagagga gaattcaaga   1320
ctccttcaag agcgtggcgt ggcttatatt aatgctgact catctataga aggaaactac   1380
actctgagag ttgattgtac accgctgatg tacagcttgg tacacaacct aacaaaagag   1440
ctgaaaagcc ctgatgaagg ctttgaaggc aaatctcttt atgaaagttg gactaaaaaa   1500
agtccttccc cagagttcag tggcatgccc aggataagca aattgggatc tggaaatgat   1560
tttgaggtgt tcttccaacg acttggaatt gcttcaggca gcacggta tactaaaaat     1620
tgggaaacaa acaaattcag cggctatcca ctgtatcaca gtgtctatga acatatgag    1680
ttggtggaaa agttttatga tccaatgttt aaatatcacc tcactgtggc ccaggttcga   1740
ggagggatgg tgtttgagct agccaattcc atagtgctcc cttttgattg tcgagattat   1800
gctgtagttt taagaaagta tgctgacaaa atctacagta tttctatgaa acatccacag   1860
gaaatgaaga catacagtgt atcatttgat tcacttttttt ctgcagtaaa gaattttaca   1920
gaaattgctt ccaagttcag tgagagactc caggactttg acaaaagcaa cccaatagta   1980
ttaagaatga tgaatgatca actcatgttt ctggaaagag catttattga tccattaggg   2040
ttaccagaca ggcctttta taggcatgtc atctatgctc caagcagcca caacaagtat    2100
gcaggggagt cattcccagg aatttatgat gctctgtttg atattgaaag caaagtggac   2160
ccttccaagg cctggggaga agtgaagaga cagatttatg ttgcagcctt cacagtgcag   2220
gcagctgcag agactttgag tgaagtagcc taa                                2253
```

<210> SEQ ID NO 2
<211> LENGTH: 750
<212> TYPE: PRT
<213> ORGANISM: Homo sapiens
<400> SEQUENCE: 2

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
```

```
            115                 120                 125
Ser Ile Ile Asn Glu Asp Gly Asn Glu Ile Phe Asn Thr Ser Leu Phe
130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
                195                 200                 205

Phe Arg Gly Asn Lys Val Lys Asn Ala Gln Leu Ala Gly Ala Lys Gly
                210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                    245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Ile Ala Glu Ala Val Gly
                275                 280                 285

Leu Pro Ser Ile Pro Val His Pro Ile Gly Tyr Tyr Asp Ala Gln Lys
290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                    325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
                355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                    405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
                435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
                515                 520                 525

Gly Ile Ala Ser Gly Arg Ala Arg Tyr Thr Lys Asn Trp Glu Thr Asn
530                 535                 540
```

```
Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
            565                 570                 575

Ala Gln Val Arg Gly Gly Met Val Phe Glu Leu Ala Asn Ser Ile Val
        580                 585                 590

Leu Pro Phe Asp Cys Arg Asp Tyr Ala Val Val Leu Arg Lys Tyr Ala
    595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Glu Thr Leu Ser Glu Val Ala
            740                 745                 750

<210> SEQ ID NO 3
<211> LENGTH: 18
<212> TYPE: PRT
<213> ORGANISM: Artificial Sequence
<220> FEATURE:
<223> OTHER INFORMATION: PSMA epitope

<400> SEQUENCE: 3

Cys Asn Ile Thr Pro Lys His Asn Met Lys Ala Phe Leu Asp Glu Leu
1               5                   10                  15

Lys Ala

<210> SEQ ID NO 4
<211> LENGTH: 19
<212> TYPE: PRT
<213> ORGANISM: Artificial Sequence
<220> FEATURE:
<223> OTHER INFORMATION: PSMA epitope

<400> SEQUENCE: 4

Cys Gly Thr Glu Gln Asn Phe Gln Leu Ala Lys Gln Ile Gln Ser Gln
1               5                   10                  15

Trp Lys Glu

<210> SEQ ID NO 5
<211> LENGTH: 16
<212> TYPE: PRT
<213> ORGANISM: Artificial Sequence
<220> FEATURE:
<223> OTHER INFORMATION: PSMA epitope

<400> SEQUENCE: 5

Cys Gly Leu Asp Ser Val Glu Leu Ala His Tyr Asp Val Leu Leu Ser
```

```
                1               5                  10                 15

<210> SEQ ID NO 6
<211> LENGTH: 14
<212> TYPE: PRT
<213> ORGANISM: Artificial Sequence
<220> FEATURE:
<223> OTHER INFORMATION: PSMA epitope

<400> SEQUENCE: 6

Cys Phe Ser Ala Phe Ser Pro Gln Gly Met Pro Glu Gly Asp
1               5                   10

<210> SEQ ID NO 7
<211> LENGTH: 11
<212> TYPE: PRT
<213> ORGANISM: Artificial Sequence
<220> FEATURE:
<223> OTHER INFORMATION: PSMA epitope

<400> SEQUENCE: 7

Cys Ala Pro Gly Val Lys Ser Tyr Pro Asp Gly
1               5                   10

<210> SEQ ID NO 8
<211> LENGTH: 12
<212> TYPE: PRT
<213> ORGANISM: Artificial Sequence
<220> FEATURE:
<223> OTHER INFORMATION: PSMA epitope

<400> SEQUENCE: 8

Cys Ala Tyr Arg Arg Gly Ile Ala Glu Ala Val Gly
1               5                   10

<210> SEQ ID NO 9
<211> LENGTH: 11
<212> TYPE: PRT
<213> ORGANISM: Artificial Sequence
<220> FEATURE:
<223> OTHER INFORMATION: PSMA epitope

<400> SEQUENCE: 9

Cys His Ile His Ser Thr Asn Glu Val Thr Arg
1               5                   10

<210> SEQ ID NO 10
<211> LENGTH: 12
<212> TYPE: PRT
<213> ORGANISM: Artificial Sequence
<220> FEATURE:
<223> OTHER INFORMATION: PSMA epitope

<400> SEQUENCE: 10

Cys Gly Lys Ser Leu Tyr Glu Ser Trp Thr Lys Lys
1               5                   10

<210> SEQ ID NO 11
<211> LENGTH: 16
<212> TYPE: PRT
<213> ORGANISM: Artificial Sequence
<220> FEATURE:
<223> OTHER INFORMATION: PSMA epitope

<400> SEQUENCE: 11

Cys Ala Ser Gly Arg Ala Arg Tyr Thr Lys Asn Trp Glu Thr Asn Lys
1               5                   10                  15
```

```
<210> SEQ ID NO 12
<211> LENGTH: 18
<212> TYPE: PRT
<213> ORGANISM: Artificial Sequence
<220> FEATURE:
<223> OTHER INFORMATION: PSMA epitope

<400> SEQUENCE: 12

Cys Leu Tyr His Ser Val Tyr Glu Thr Tyr Glu Leu Val Glu Lys Phe
1               5                   10                  15

Tyr Asp

<210> SEQ ID NO 13
<211> LENGTH: 13
<212> TYPE: PRT
<213> ORGANISM: Artificial Sequence
<220> FEATURE:
<223> OTHER INFORMATION: PSMA epitope

<400> SEQUENCE: 13

Cys Ala Asp Lys Ile Tyr Ser Ile Ser Met Lys His Pro
1               5                   10

<210> SEQ ID NO 14
<211> LENGTH: 19
<212> TYPE: PRT
<213> ORGANISM: Artificial Sequence
<220> FEATURE:
<223> OTHER INFORMATION: PSMA epitope

<400> SEQUENCE: 14

Cys Cys Ser Glu Arg Leu Gln Asp Phe Glu Lys Ser Asn Pro Ile Val
1               5                   10                  15

Leu Arg Cys

<210> SEQ ID NO 15
<211> LENGTH: 10
<212> TYPE: PRT
<213> ORGANISM: Artificial Sequence
<220> FEATURE:
<223> OTHER INFORMATION: PSMA epitope

<400> SEQUENCE: 15

Cys Glu Ser Lys Val Asp Pro Ser Lys Ala
1               5                   10

<210> SEQ ID NO 16
<211> LENGTH: 14
<212> TYPE: PRT
<213> ORGANISM: Artificial Sequence
<220> FEATURE:
<223> OTHER INFORMATION: PSMA epitope

<400> SEQUENCE: 16

Cys Thr Val Gln Ala Ala Ala Glu Thr Leu Ser Glu Val Ala
1               5                   10

<210> SEQ ID NO 17
<211> LENGTH: 8
<212> TYPE: PRT
<213> ORGANISM: Artificial Sequence
<220> FEATURE:
<223> OTHER INFORMATION: peptide mimetope

<400> SEQUENCE: 17

Lys Gln Ser Tyr Asn Phe Ile Thr
```

<210> SEQ ID NO 18
<211> LENGTH: 6
<212> TYPE: PRT
<213> ORGANISM: Artificial Sequence
<220> FEATURE:
<223> OTHER INFORMATION: peptide mimetope

<400> SEQUENCE: 18

Gly Gly Phe Pro Tyr Gly
1               5

<210> SEQ ID NO 19
<211> LENGTH: 6
<212> TYPE: PRT
<213> ORGANISM: Artificial Sequence
<220> FEATURE:
<223> OTHER INFORMATION: peptide mimetope

<400> SEQUENCE: 19

Gly Phe Pro Tyr Gly Gly
1               5

<210> SEQ ID NO 20
<211> LENGTH: 7
<212> TYPE: PRT
<213> ORGANISM: Artificial Sequence
<220> FEATURE:
<223> OTHER INFORMATION: peptide mimetope

<400> SEQUENCE: 20

Leu Gly Arg Pro Phe Ala His
1               5

<210> SEQ ID NO 21
<211> LENGTH: 7
<212> TYPE: PRT
<213> ORGANISM: Artificial Sequence
<220> FEATURE:
<223> OTHER INFORMATION: peptide mimetope

<400> SEQUENCE: 21

Leu Gly Arg Gly Phe Ala His
1               5

<210> SEQ ID NO 22
<211> LENGTH: 7
<212> TYPE: PRT
<213> ORGANISM: Artificial Sequence
<220> FEATURE:
<223> OTHER INFORMATION: peptide mimetope

<400> SEQUENCE: 22

Gly Gly Arg Pro Phe Gly Gly
1               5

<210> SEQ ID NO 23
<211> LENGTH: 14
<212> TYPE: PRT
<213> ORGANISM: Artificial Sequence
<220> FEATURE:
<223> OTHER INFORMATION: peptide mimetope

<400> SEQUENCE: 23

Gly Glu Asn Tyr Tyr Thr Ser Arg Tyr Gly Phe Phe Asp Val
1               5                   10

<210> SEQ ID NO 24
<211> LENGTH: 10
<212> TYPE: PRT
<213> ORGANISM: Artificial Sequence
<220> FEATURE:
<223> OTHER INFORMATION: peptide mimetope

<400> SEQUENCE: 24

Cys Lys Gln Ser Tyr Asn Phe Ile Thr Cys
1               5                   10

<210> SEQ ID NO 25
<211> LENGTH: 8
<212> TYPE: PRT
<213> ORGANISM: Artificial Sequence
<220> FEATURE:
<223> OTHER INFORMATION: peptide mimetope

<400> SEQUENCE: 25

Cys Gly Gly Phe Pro Tyr Gly Cys
1               5

<210> SEQ ID NO 26
<211> LENGTH: 8
<212> TYPE: PRT
<213> ORGANISM: Artificial Sequence
<220> FEATURE:
<223> OTHER INFORMATION: peptide mimetope

<400> SEQUENCE: 26

Cys Gly Phe Pro Tyr Gly Gly Cys
1               5

<210> SEQ ID NO 27
<211> LENGTH: 9
<212> TYPE: PRT
<213> ORGANISM: Artificial Sequence
<220> FEATURE:
<223> OTHER INFORMATION: peptide mimetope

<400> SEQUENCE: 27

Cys Leu Gly Arg Pro Phe Ala His Cys
1               5

<210> SEQ ID NO 28
<211> LENGTH: 9
<212> TYPE: PRT
<213> ORGANISM: Artificial Sequence
<220> FEATURE:
<223> OTHER INFORMATION: peptide mimetope

<400> SEQUENCE: 28

Cys Leu Gly Arg Gly Phe Ala His Cys
1               5

<210> SEQ ID NO 29
<211> LENGTH: 9
<212> TYPE: PRT
<213> ORGANISM: Artificial Sequence
<220> FEATURE:
<223> OTHER INFORMATION: peptide mimetope

<400> SEQUENCE: 29

Cys Gly Gly Arg Pro Phe Gly Gly Cys
1               5

<210> SEQ ID NO 30

```
<211> LENGTH: 16
<212> TYPE: PRT
<213> ORGANISM: Artificial Sequence
<220> FEATURE:
<223> OTHER INFORMATION: peptide mimetope

<400> SEQUENCE: 30

Cys Gly Glu Asn Tyr Tyr Thr Ser Arg Tyr Gly Phe Phe Asp Val Cys
1               5                   10                  15

<210> SEQ ID NO 31
<211> LENGTH: 9
<212> TYPE: PRT
<213> ORGANISM: Artificial Sequence
<220> FEATURE:
<223> OTHER INFORMATION: peptide mimetope

<400> SEQUENCE: 31

Cys Gly Gly Phe Pro Tyr Gly Cys Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: peptide mimetope

<400> SEQUENCE: 32

Cys Gly Phe Pro Tyr Gly Gly Cys Tyr
1               5

<210> SEQ ID NO 33
<211> LENGTH: 10
<212> TYPE: PRT
<213> ORGANISM: Artificial Sequence
<220> FEATURE:
<223> OTHER INFORMATION: peptide mimetope

<400> SEQUENCE: 33

Cys Leu Gly Arg Pro Phe Ala His Cys Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: peptide mimetope

<400> SEQUENCE: 34

Cys Leu Gly Arg Gly Phe Ala His Cys Tyr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: peptide mimetope

<400> SEQUENCE: 35

Cys Gly Gly Arg Pro Phe Gly Gly Cys Tyr
1               5                   10

<210> SEQ ID NO 36
<211> LENGTH: 10
<212> TYPE: PRT
```

```
<213> ORGANISM: Artificial Sequence
<220> FEATURE:
<223> OTHER INFORMATION: alanine mimetope

<400> SEQUENCE: 36

Cys Ala Gln Ser Tyr Asn Phe Ile Thr Cys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: alanine mimetope

<400> SEQUENCE: 37

Cys Lys Ala Ser Tyr Asn Phe Ile Thr Cys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: alanine mimetope

<400> SEQUENCE: 38

Cys Lys Gln Ala Tyr Asn Phe Ile Thr Cys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: alanine mimetope

<400> SEQUENCE: 39

Cys Lys Gln Ser Ala Asn Phe Ile Thr Cys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: alanine mimetope

<400> SEQUENCE: 40

Cys Lys Gln Ser Tyr Ala Phe Ile Thr Cys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: alanine mimetope

<400> SEQUENCE: 41

Cys Lys Gln Ser Tyr Asn Ala Ile Thr Cys
1               5                   10

<210> SEQ ID NO 42
<211> LENGTH: 10
<212> TYPE: PRT
<213> ORGANISM: Artificial Sequence
<220> FEATURE:
```

-continued

```
<223> OTHER INFORMATION: alanine mimetope

<400> SEQUENCE: 42

Cys Lys Gln Ser Tyr Asn Phe Ala Thr Cys
1               5                   10

<210> SEQ ID NO 43
<211> LENGTH: 10
<212> TYPE: PRT
<213> ORGANISM: Artificial Sequence
<220> FEATURE:
<223> OTHER INFORMATION: alanine mimetope

<400> SEQUENCE: 43

Cys Lys Gln Ser Tyr Asn Phe Ile Ala Cys
1               5                   10
```

PROSTATE CANCER DIAGNOSIS AND TREATMENT

BACKGROUND OF THE INVENTION (a) Field of the Invention

The invention relates to novel mimetopes of anti-PSMA antibodies and their use for detecting, imaging, staging, treating and monitoring of prostate cancer, and/or metastasis thereof. Furthermore, the invention also relates to novel pharmaceutical compositions for the treatment of prostate cancer.

(b) Description of Prior Art

The prostate gland is affected by various significant pathological conditions as benign growth (BPH), infection (prostatitis), and neoplasia (prostate cancer).

Prostate cancer is the second most frequently diagnosed cancer in Canadian and American men, after non-melanoma skin cancer, which is rarely fatal. More importantly, after lung cancer, prostate cancer is the most common cause of cancer-related death. The risk of developing prostate cancer increases significantly with age, particularly for men over 50. For men under 50 years of age the disease is uncommon and death from it is rare.

Prostate cancer accounts for an estimated 28% of newly diagnosed cancer in Canadian men and more than 12% of cancer-related deaths. The current lifetime risk of a Canadian man being diagnosed with prostate cancer is about 1 in 8. In the United States, prostate cancer accounts for approximately 32% of male cancer diagnoses and 14% of cancer deaths. Studies in the United States suggest that the incidence rate may be approaching 1 in 6 men.

Because the incidence of prostate cancer increases with age, it is clear that the burden of this illness will increase dramatically in the coming decades. The aging of the population, particularly the baby boomers, will have important long-term implications for the number of new cases diagnosed. Demographic trends in the next two decades will increase the population at risk for prostate cancer. Statistics Canada projections indicate that the population of men over age 50 will increase from 3.9 million in 1999 to 5.6 million in 2011 (44% increase) and 6.3 million in 2016 (62% increase). The United States Census Bureau projections indicate that the population of men over age 50 will increase from 33.8 million in 1999 to 45.8 million in 2011 (36% increase) and 50.7 million in 2016 (50% increase).

As a consequence of the expected increases in the number of cases of prostate cancer in the coming years due to rising incidence rates and the aging North American population, more resources will likely be allocated to screening men over 50 for this condition, therefore yielding an increase in the number of cases of identified prostate cancer.

Prostate cancer often exhibits a long latency period. However, it is believed that prostate cancer often remains undetected. Also, because it possesses a high metastatic potential to bone and the lymph nodes, with <10% of individuals diagnosed with prostate cancer also demonstrated, by radionuclide scans, to have bone metastasis, prompt detection and treatment is needed to limit mortality caused by this disease. A recent review of treatment of prostate cancer is by Pirtskhalaishvilig et al. (2001, *Cancer Practice* 9(6):295).

Increased detection of prostate cancer is due in part to increased awareness and the widespread use of clinical markers such as prostate specific antigen (PSA). Prostate specific antigen is a protein that is produced in very high concentrations in prostate cancer cells. Cancer development results in an altered and subsequent loss of normal gland architecture. This in turn leads to an inability to remove secretions and thus the secretions reach the serum. Serum PSA measurement is one method for screening for prostate cancer.

The current diagnostic and treatment paradigm for prostate cancer is reflected in Clinical Practice Guidelines that are widely available to practicing physicians. The guidelines presented below outline the common approach to the detection and management of prostate cancer.

The Prostate Specific Antigen test is a blood test used to detect prostate cancer in the earliest stages and should be offered annually to men 50 and older with a life expectancy of 10 years or more, and to younger men at high risk for prostate cancer.

The Digital Rectal Exam (DRE) is a test that helps to identify cancer of the prostate, and should be performed on men who are 50 and older and to younger men at high risk for prostate cancer.

A biopsy is recommended for all men who have an abnormal PSA or DRE.

The options for primary management of prostate cancer are surgery, radiation therapy or close observation. Treatment decisions are based on the aggressiveness of the cancer, the stage of the cancer and the life expectancy of the individual.

Advanced prostate cancer is best managed with hormone therapy.

Radiation therapy can include external and implanted seeds, a procedure known as brachytherapy.

The PSA test, which facilitates early detection of prostate cancer, has been available in Canada since 1986, although its use did not become widespread until the early 1990's. In 1994 the U.S. Food and Drug Administration (FDA) approved the use of the PSA test in conjunction with DRE as an aid in detecting prostate cancer. The free PSA test (fPSA), a more sensitive test for prostate cancer risk than the standard PSA test, received FDA approval in 1998.

Because of the limitations of the PSA test (lack of specificity for prostate cancer and a significant number of "false positive" and "false negative" test results) it remains an investigational tool as opposed to an absolute diagnostic test.

Prostate biopsies are performed to confirm the presence of cancer cells following suspicion raised by the DRE or a positive PSA test. The most commonly reported complications of biopsy consist of traces of blood in the urine, semen or feces. Prostatic biopsy represents the cornerstone of prostate cancer diagnosis.

For prostate cancers in general, biopsies miss cancers at a rate estimated as high as 50 percent. Furthermore, even if a cancer is detected, the location and staging of cancerous cells are not adequately identified.

Thus, there is a need for an improved method for diagnosis and/or detection of cancerous prostate cells.

An important prognostic factor is prostate cancer stage. Cancer staging is performed to determine the extent and spread of cancer in the prostate. Prostate cancer metastasizes by local spread to the pelvic lymph nodes, seminal vesicles, urinary bladder, or pelvic side walls and to distant sites such as bone, lung, liver, or adrenals.

The cancer foci have different malignant potentials and do not pose equal risks for the individual. Heterogeneity confounds the interpretation of positive prostate biopsies since it is not possible to be certain that the most clinically relevant foci of cancer have been detected.

Approximately only 30% of early stage disease will progress to clinically relevant disease within the lifetime of the individual. It is therefore critical to be able to identify those individuals at risk of progression who would benefit from aggressive therapy while sparing low-risk individuals the morbidity resulting from aggressive treatment of indolent disease. Neither rising PSA nor the presence of cancer cells on biopsy may indicate definitively the presence of lethal disease.

A new prostate imaging technology that provides for accurate visualization of extraprostatic growth indicative of metastasis would provide physicians with a tool to determine the progression of the cancer and would be extremely valuable in directing treatment options. Spectroscopy significantly improves the diagnosis of extracapsular extension by MRI. However, studies demonstrate that there is high variability in how clinicians interpret the significance of extracapsular extension. Both CT and MRI can be helpful in staging prostate cancer, because they can indicate periprostatic cancer spread, lymph node abnormality and bone involvement, but their sensitivity for revealing cancer extension has limitations.

Thus, there is a need for a non-invasive test that is able to identify lymph node metastases in individuals at risk for extraprostatic disease following the detection of elevated PSA and/or abnormal DRE and a positive biopsy. This will allow clinicians to reliably differentiate individuals with organ-confined disease from those with metastatic spread to lymph nodes. This will provide the opportunity for the individual and physician to make an informed decision on how to treat the disease and will significantly improve individual health outcome.

Furthermore, a new technology that is able to localize cancerous prostate cells that remain following radical prostatectomy would assist physicians in removing all of the cancerous cells from an individual's body with focused treatment such as radiation therapy. A labeled technology that selectively binds prostate cancer cells will allow clinicians to localize any remaining cancer cells following surgery. An additional new technology would provide direct delivery of therapeutic agents, perhaps preventing the need for surgery.

Thus, there is a need for an improved method to detect and/or diagnose lymph node metastases in individuals at risk for extraprostatic disease following the detection of elevated PSA and/or abnormal DRE and a positive biopsy.

A substantial amount of work has been put into identifying enzyme or antigen markers, which could be used as sites for detection and/or diagnosis for various types of cancers. These markers could also be used to target cancer cells for treatment with therapeutic and/or cancer cell killing agents. The ideal cancer marker would exhibit, among other characteristics, tissue or cell-type specificity.

A 750 amino acid protein (FIG. 2; SEQ ID NO:2), prostate-specific membrane antigen (PSMA), localized to the prostatic membrane has been identified. The complete coding sequence of the gene (FIG. 1; nucleotides 262 to 2514 of GenBank™ accession number NM_004476) is presented as SEQ ID NO:1. PSMA is an integral Type II membrane glycoprotein with a short intracellular tail and a long extracellular domain. This antigen was identified as the result of generating monoclonal antibodies to a prostatic cancer cell, LNCaP (Horoszewicz et al. (1983) Cancer Res. 43:1809-1818). Israeli et al. (Israeli et al. (1993) Cancer Res. 53:227-230) describes the cloning and sequencing of PSMA and reports that PSMA is predominantly expressed in prostate derived cells and shows increased expression levels in metastatic sites and in hormone-refractory states. Other studies have indicated that PSMA is more strongly expressed in prostate cancer cells relative to cells from the normal prostate or from a prostate with benign hyperplasia. Current methods of targeting prostate specific membrane antigen use antibodies with binding specificity to PSMA. One of the first antibodies described with binding specificity to PSMA was 7E11 (Horoszewicz et al. (1987) Anticancer Res. 7:927-936 and U.S. Pat. No. 5,162,504). Indium-labeled 7E11 localizes to both prostate and sites of metastasis, and is more sensitive for detecting cancer sites than either CT or MR imaging, or bone scan (Bander (1994) Sem. In Oncology 21:607-612).

One of the major disadvantages of the 7E11 antibody is that it is specific to the portion of the PSMA molecule which is present on the inside of the cell (intracellular). Antibody molecules do not normally cross the cell membrane, unless they bind to an extracellular antigen, which subsequently becomes internalized. As such, 7E11 cannot be used to target a living prostate cell, cancerous or otherwise. The use of 7E11 for detection or imaging is therefore limited to pockets of dead cells within cancers or tissues with large amounts of dead cells, which cells render available their intracellular portion of PSMA for binding with this antibody.

U.S. Pat. No. 6,107,090, in the name of Neil Bander, and U.S. Pat. No. 6,150,508, in the name of Gerald Murphy et al. describe numerous monoclonal antibodies which recognize the extracellular domain of PSMA, thereby overcoming one of the major drawbacks of the 7E11 antibody. These antibodies, being able to bind to the extracellular domain of PSMA are capable of binding to living prostate cells, thereby allowing a more effective method of diagnosis than 7E11.

As described above, antibodies to PSMA are already in use for diagnostic purposes. For example, PSMA is the antigen recognized by the targeting monoclonal antibody used in ProstaScint™, Cytogen's imaging agent for prostate cancer. However, despite the benefits of antibodies, they possess several drawbacks which make them less than ideal for use in methods of detection, diagnosis and/or treatment of prostate cancers. Specifically, antibodies are high molecular weight proteins in the 150 kDa range and therefore display poor tissue penetrability. Furthermore, mouse monoclonal antibodies act as antigenic targets for the immune system, which results in biological instability in vivo.

It would be highly desirable to be provided with a small molecule, such as a mimetope to overcome the drawbacks of antibodies (Ab) as detailed above, but that retain similar high specificity and affinity of monoclonal antibodies (mAb). A mimetope is a synthetic binding agent and/or derivatives thereof having binding characteristics which imitate or mimic the binding characteristics of a molecule, including a protein and an antibody, The use of mimetopes presents advantages over the use of antibodies for detection, diagnosis and/or treatment of prostate cancer because of their accessibility to cancer sites. Mimetopes eliminate the problems inherent in using, for example, mouse monoclonal antibodies in humans. Mouse monoclonal antibodies induce antibodies that will clear xenogenic antibodies used for detection, diagnosis and/or treatment of prostate cancer.

It would be highly desirable to be provided with an improved method for diagnosis and/or detection of cancerous prostate cells.

It would be highly desirable to be provided with a new prostate imaging technology offering accurate visualization of extraprostatic growth indicative of metastasis which would provide physicians with a tool to determine the progression of the cancer and be extremely valuable in directing treatment options.

It would be highly desirable to be provided with a non-invasive test that is able to identify lymph node metastases in individuals at risk for extraprostatic disease following the detection of elevated PSA and/or abnormal DRE and a positive biopsy.

It would be highly desirable to be provided with an imaging technology that decreases morbidity by identifying individuals in which surgery is not indicated.

It would be highly desirable to be provided with a new technology that is able to localize cancerous prostate cells that remain following radical prostatectomy which would assist physicians in removing all of the cancerous cells from an individual's body. In addition, it would be highly desirable to be provided with a new technology which would provide direct delivery of therapeutic agents, perhaps preventing the need for surgery.

It would be highly desirable to be provided with an improved method to detect and/or diagnose lymph node metastases in individuals at risk for extraprostatic disease following the detection of elevated PSA.

It would be highly desirable to be provided with an improved molecule over antibodies which would possess characteristics able to overcome the drawbacks and disadvantages present with antibodies.

It would be highly desirable to be provided with a new prostate imaging technology that provides for accurate visualization of extraprostatic growth indicative of metastasis which would provide physicians with a tool to determine the progression of the cancer and be extremely valuable in directing treatment options.

It would be highly desirable to be provided with novel mimetopes of anti-PSMA monoclonal antibodies and their use for detecting, imaging, staging, treating and monitoring of prostate cancer, and/or metastasis thereof. It would also be highly desirable to be provided with novel pharmaceutical compositions for the treatment of prostate cancer.

SUMMARY OF THE INVENTION

One aim of the present invention is to provide novel mimetopes of anti-PSMA antibodies and their use for detecting, imaging, staging, treating and monitoring of prostate cancer, and/or metastasis thereof.

Another aim of the present invention is to provide novel pharmaceutical compositions for the treatment of prostate cancer.

In accordance with another embodiment of the present invention there is provided the use of an isolated monoclonal antibody or antigen binding fragment thereof which binds to PSMA for the design of a mimetope, wherein the mimetope binds to PSMA.

In a preferred use of the present invention the monoclonal antibody or antigen binding fragment thereof binds to an epitope of the extracellular region of PSMA according to the present invention.

In accordance with another embodiment of the present invention there is provided a method of designing a mimetope which binds to an epitope of PSMA, comprising determining a region of an antibody which binds to the epitope responsible for the binding; and designing the mimetope based on the region.

In accordance with another embodiment of the present invention there is provided a mimetope which binds to PSMA.

In accordance with another embodiment of the present invention there is provided a mimetope which binds to an extracellular region of PSMA.

In accordance with another embodiment of the present invention there is provided a mimetope which binds to an extracellular region of PSMA, ranging between amino acid 51 to amino acid 67, amino acid 85 to amino acid 102, amino acid 104 to amino acid 118, amino acid 161 to amino acid 173, amino acid 236 to amino acid 245, amino acid 278 to amino acid 288, amino acid 345 to amino acid 354, amino acid 490 to amino acid 500, amino acid 531 to amino acid 545, amino acid 551 to amino acid 567, amino acid 608 to amino acid 619, amino acid 649 to amino acid 660, amino acid 716 to amino acid 724, or amino acid 738 to amino acid 750 which comprises an amino acid sequence selected from the group consisting of SEQ ID NOs: 3-16, respectively.

In accordance with another embodiment of the present invention there is provided a mimetope, which comprises one of the following formula I to IV:

$$X\text{-}A_1\text{-}A_2\text{-}A_3\text{-}A_4\text{-}A_5\text{-}A_6\text{-}A_7\text{-}A_8\text{-}Y \quad\quad\quad I$$

wherein,

X is $NH_2$— for a linear mimetope, one or more amino acid residue or a moiety linking $A_1$ with $A_8$ for a cyclic mimetope;

$A_1$ is an amino acid selected from the group consisting of Lys, Trp, Arg, Gln, Glu and Tyr;

$A_2$-$A_3$ is a chemical spacer of a size corresponding to that of two amino acids or any two amino acids; or $A_2$ is an amino acid selected from the group consisting of Glu and Asp and $A_3$ is an amino acid selected from the group consisting of Ser and Thr;

$A_4$ is an amino acid selected from the group consisting of Tyr, Trp and Phe;

$A_5$ is an amino acid selected from the group consisting of Asn, Gln and His;

$A_6$ is an amino acid selected from the group consisting of Phe, Met, Leu and Tyr;

$A_7$ is an amino acid selected from the group consisting of Ile, Leu and Val;

$A_8$ is a chemical spacer of a size corresponding to that of one amino acid or any amino acid; or is an amino acid selected from the group consisting of Thr and Ser; and Y is COOH—, one or more amino acid residue or a moiety linking $A_1$ with $A_8$ creating a cyclic mimetope;

$$X\text{-}A_{1'}\text{-}A_{2'}\text{-}A_{3'}\text{-}A_{4'}\text{-}A_{5'}\text{-}A_{6'}\text{-}Y \quad\quad\quad II$$

wherein,

X is $NH_2$— for a linear mimetope, one or more amino acid residue or a moiety linking $A_1$ with $A_8$ for a cyclic mimetope;

$A_{1'}$ is a chemical spacer of a size corresponding to that of one amino acid; or any amino acid; or an amino acid selected from the group consisting of Gly, Ala and Pro;

$A_{2'}$ is an amino acid selected from the group consisting of Gly, Ala, Pro, Phe, Met, Leu and Tyr;

$A_{3'}$ is an amino acid selected from the group consisting of Phe, Met, Leu, Tyr, Pro, Ala and Gly;

$A_{4'}$ is an amino acid selected from the group consisting of Pro, Ala, Gly, Tyr, Trp and Phe;

$A_{5'}$ is an amino acid selected from the group consisting of Tyr, Trp, Phe, Gly, Ala and Pro;

$A_{6'}$ is a chemical spacer of a size corresponding to that of one amino acid; or any amino acid; or an amino acid selected from the group consisting of Gly, Ala and Pro; and Y is COOH—, one or more amino acid residue or a moiety linking $A_1$ with $A_8$ creating a cyclic mimetope;

$$X\text{-}A_{1''}\text{-}A_{2''}\text{-}A_{3''}\text{-}A_{4''}\text{-}A_{5''}\text{-}A_{6''}\text{-}A_{7''}\text{-}Y \quad\quad\quad III$$

wherein,

X is $NH_2$— for a linear mimetope, one or more amino acid residue or a moiety linking $A_1$ with $A_8$ for a cyclic mimetope;

$A_{1''}$ is an amino acid selected from the group consisting of Leu, Ile, Val, Gly, Ala and Pro;

A$_{2''}$ is a chemical spacer of a size corresponding to that of one amino acid; or any amino acid; or an amino acid selected from the group consisting of Gly, Ala and Pro;
A$_{3''}$ is an amino acid selected from the group consisting of Arg and Lys;
A$_{4''}$ is an amino acid selected from the group consisting of Pro, Ala, and Gly;
A$_{5''}$ is an amino acid selected from the group consisting of Phe, Met, Leu and Tyr;
A$_{6''}$ is an amino acid selected from the group consisting of Ala, Gly, Ser and Pro;
A$_{7''}$ is an amino acid selected from the group consisting of His, Asn, Gln, Gly, Ala and Pro; and
Y is COOH—, one or more amino acid residue or a moiety linking A$_1$ with A$_8$ creating a cyclic mimetope; and

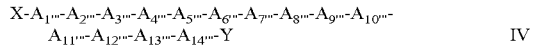   IV wherein,
X is NH$_2$— for a linear mimetope, one or more amino acid residue or a moiety linking A$_1$ with A$_8$ for a cyclic mimetope;
A$_{1'''}$ is a chemical spacer of a size corresponding to that of one amino acid; or any amino acid; or an amino acid selected from the group consisting of Gly, Ala and Pro;
A$_{2'''}$ is an amino acid selected from the group consisting of Glu and Asp;
A$_{3'''}$ is an amino acid selected from the group consisting of Asp and Glu;
A$_{4'''}$ is an amino acid selected from the group consisting of Tyr, Trp and Phe;
A$_{5'''}$ is an amino acid selected from the group consisting of Tyr, Trp and Phe;
A$_{6'''}$ is an amino acid selected from the group consisting of Thr and Ser;
A$_{7'''}$ is an amino acid selected from the group consisting of Ser and Thr;
A$_{8'''}$ is an amino acid selected from the group consisting of Arg and Lys;
A$_{9'''}$ is an amino acid selected from the group consisting of Tyr, Trp and Phe;
A$_{10'''}$ is a chemical spacer of a size corresponding to that of one amino acid; or any amino acid; or an amino acid selected from the group consisting of Gly, Ala and Pro;
A$_{11'''}$ is an amino acid selected from the group consisting of Phe, Met, Leu and Tyr;
A$_{12'''}$ is an amino acid selected from the group consisting of Phe, Met, Leu and Tyr;
A$_{13'''}$ is an amino acid selected from the group consisting of Asp and Glu;
A$_{14'''}$ is an amino acid selected from the group consisting of Val, Ile and Leu; and
Y is COOH—, one or more amino acid residue or a moiety linking A$_1$ with A$_8$ creating a cyclic mimetope.

In accordance with a preferred embodiment of the present invention there is provided a mimetope, wherein X and Y are Cys, whereby forming a disulfide bridge and a cyclic mimetope.

The preferred mimetope in accordance with the present invention has an amino acid sequence selected from the group consisting of:

```
LysGluSerTyrAsnPheIleThr;           (SEQ ID NO: 17)

GlyGlyPheProTyrGly;                 (SEQ ID NO: 18)

GlyPheProTyrGlyGly;                 (SEQ ID NO: 19)

LeuGlyArgProPheAlaHis;              (SEQ ID NO: 20)

LeuGlyArgGlyPheAlaHis;              (SEQ ID NO: 21)

GlyGlyArgProPheGlyGly;              (SEQ ID NO: 22)

GlyGluAspTyrTyrThrSerArgTyrGlyPhe   (SEQ ID NO: 23)
PheAspVal;

CysLysGluSerTyrAsnPheIleThrCys;     (SEQ ID NO: 24)

CysGlyGlyPheProTyrGlyCys;           (SEQ ID NO: 25)

CysGlyPheProTyrGlyGlyCys;           (SEQ ID NO: 26)

CysLeuGlyArgProPheAlaHisCys;        (SEQ ID NO: 27)

CysLeuGlyArgGlyPheAlaHisCys;        (SEQ ID NO: 28)

CysGlyGlyArgProPheGlyGlyCys;        (SEQ ID NO: 29)

CysGlyGluAspTyrTyrThrSerArgTyrGly   (SEQ ID NO: 30)
PhePheAspValCys;

CysGlyGlyPheProTyrGlyCysTyr;        (SEQ ID NO: 31)

CysGlyPheProTyrGlyGlyCysTyr;        (SEQ ID NO: 32)

CysLeuGlyArgProPheAlaHisCysTyr;     (SEQ ID NO: 33)

CysLeuGlyArgGlyPheAlaHisCysTyr;     (SEQ ID NO: 34)
and

CysGlyGlyArgProPheGlyGlyCysTyr.     (SEQ ID NO: 35)
```

In accordance with another embodiment of the present invention there is provided a pharmaceutical composition for targeted treatment of prostate cancer, and/or metastasis with PSMA thereon, which comprises a mimetope according to the present invention bound to a cytotoxic drug in association with a pharmaceutically acceptable carrier, wherein the PSMA binding site of the mimetope is available for targeted binding of PSMA and the cytotoxic drug remains biologically active.

In accordance with another embodiment of the present invention there is provided a composition for detection of prostate cancer, and/or metastasis thereof with PSMA thereon in an individual and/or in a sample obtained therefrom, which comprises a mimetope according to the present invention bound to a detectable label in association with a physiologically acceptable carrier or an in vitro acceptable carrier, wherein the PSMA binding site of the mimetope is available for binding to PSMA and the detectable label remains detectable.

In accordance with another embodiment of the present invention there is provided a use of the method of the present invention, to indicate the location of prostate cancer, and/or metastasis thereof within the individual or a sample obtained therefrom.

In accordance with another embodiment of the present invention there is provided an assay system for detecting prostate cancer, and/or metastasis thereof comprising a labeled mimetope according to the present invention.

A preferred assay system for detecting prostate cancer, and/or metastasis thereof of the present invention further comprises means for quantifying an amount of antigen bound to the mimetope, wherein an amount of antigen bound to the mimetope above a predetermined level is indicative of prostate cancer, and/or metastasis thereof.

A preferred assay system of the present invention further comprises a multi-well microplate including the mimetope in at least one well.

In a preferred assay system of the present invention the mimetope binds to a peptide selected from the group consisting of PSMA, an extracellular region of PSMA, a peptide corresponding to an extracellular region of PSMA or SEQ ID NOs: 3-16 in Table 1 below.

TABLE 1

Sequence of PSMA antigens

| Ref. No. | Peptide Sequence[a] | Location | SEQ ID NO |
|---|---|---|---|
| 4243 | NH$_2$-CysAsnIleThrProLysHisAsnMet LysAlaPheLeuAspGluLeuLysAla-COOH | 51-67 | 3 |
| 4244 | NH$_2$-CysGlyThrGluGlnAsnPheGlnLeu AlaLysGlnIleGlnSerGlnTrpLysGlu-COOH | 85-102 | 4 |
| PS0210 | NH$_2$-CysGlyLeuAspSerValGluLeuAla HisTyrAspValLeuLeuSer-COOH | 104-118 | 5 |
| PS0211 | NH$_2$-CysPheSerAlaPheSerProGlnGly MetProGluGlyAsp-COOH | 161-173 | 6 |
| PS0212 | NH$_2$-CysAlaProGlyValLysSerTyrPro AspGly-COOH | 236-245 | 7 |
| PS0213 | NH$_2$-CysAlaTyrArgArgGlyIleAlaGlu AlaValGly-COOH | 278-288 | 8 |
| PS0214 | NH$_2$-CysHisIleHisSerThrAsnGluVal ThrArg-COOH | 345-354 | 9 |
| PS0215 | NH$_2$-CysGlyLysSerLeuTyrGluSerTrp ThrLysLys-COOH | 490-500 | 10 |
| 4245 | NH$_2$-CysAlaSerGlyArgAlaArgTyrThr LysAsnTrpGluThrAsnLys-COOH | 531-545 | 11 |
| 4246 | NH$_2$-CysLeuTyrHisSerValTyrGluThr TyrGluLeuValGluLysPheTyrAsp-COOH | 551-567 | 12 |
| PS0216 | NH$_2$-CysAlaAspLysIleTyrSerIleSer MetLysHisPro-COOH | 608-619 | 13 |
| PS0217 | NH$_2$-Cys-CysSerGluArgLeuGlnAspPhe GluLysSerAsnProIleValLeuArgCys-COOH | 649-660 | 14 |
| PS0218 | NH$_2$-CysGluSerLysValAspProSerLys Ala-COOH | 716-724 | 15 |
| PS0219 | NH$_2$-CysThrValGlnAlaAlaAlaGluThr LeuSerGluValAla-COOH | 738-750 | 16 |

[a]N-terminal Cys residues on each peptide are optionally added for manipulation and/or coupling; they are not part of the PSMA sequence. The Cys residues at the N-terminal and C-terminal of PS0217 also allow for the potential for cyclisation.

In accordance with another embodiment of the present invention there is provided a method of determining relative efficacy of a therapeutic regimen to be performed on an individual suffering from and/or being treated for prostate cancer, and/or metastasis thereof, the method comprising: (a) initially analyzing the individual or a biological sample obtained therefrom to determine presence of cancer-associated antigen able to bind with the mimetope according to the present invention and (b) periodically repeating step (a) during treatment of the individual to determine increase or decrease in quantity of cancer-associated antigen present in the sample.

In accordance with another embodiment of the present invention there is provided a use of a mimetope according to the present invention as a probe for screening a library of molecules, agents, proteins, peptides and/or chemicals to identify a molecule, agent, protein, peptide and/or chemical able to bind to the mimetope.

In a preferred use of a mimetope of the present invention the library is a chemical library, antibody library, phage display library, peptide library or library of natural compounds.

In a preferred use of a mimetope of the present invention the molecule, agent, protein, peptide and/or chemical is an antagonist or agonist of PSMA.

In a preferred use of a mimetope of the present invention the protein is an antibody and or antigen binding portion thereof.

In accordance with another embodiment of the present invention there is provided a use of a mimetope of the present invention for designing a chemical ligand binding to PSMA, an extracellular portion of PSMA or peptides thereof.

For the purpose of the present invention the following terms are defined below.

The term "cancer" is intended to mean any cellular malignancy whose unique trait is the loss of normal controls which results in unregulated growth, lack of differentiation and ability to invade local tissues and metastasize. Cancer can develop in any tissue of any organ. More specifically, cancer is intended to include, without limitation, prostate cancer, leukemia, hormone dependent cancers, breast cancer, colon cancer, lung cancer, epidermal cancer, liver cancer, esophageal cancer, stomach cancer.

The term "prostate cancer" is intended to mean an uncontrolled (malignant) growth of cells in the prostate gland, which is located at the base of the urinary bladder and is responsible for helping control urination as well as forming part of the semen.

The term "metastasis" is intended to mean cancer that has spread beyond the prostate. "Metastasis" is also intended to mean the process by which cancer spreads from one part of the body to another, the way it travels from the place at which it first arose as a primary tumor to distant locations in the body.

The term "mimetope" is intended to mean a synthetic binding agent and/or derivatives thereof having binding characteristics which imitate or mimic the binding characteristics of a molecule, including a protein and an antibody. A mimetope can be a peptide that has been modified to decrease its susceptibility to degradation but that still retains binding activity. Other examples of mimetopes include, but are not limited to, totally synthetic molecules, amino acid-based compounds, protein-based compounds, carbohydrate-based compounds, lipid-based compounds, nucleic acid-based compounds, natural organic compounds, or synthetically derived organic compounds, including synthetically derived peptides and organic peptidomimetics. A mimetope or synthetic binding agent can be obtained by, for example, identifying the complementary determining regions (CDRs) of an antibody.

Each antibody is composed of a pair of heavy and a pair of light molecular-weight polypeptide chain, called heavy or H chain, and light or L chain. The chains that form the immunoglobulin G (IgG) molecule are divided into domains, 4 in the H chains and 2 in the L chains. Within each domain, folding of the polypeptide chain produced two parallel planes, each containing several segments running in opposite direction and folded into beta structure. The N-terminal domain of the IgG molecules is characterized by sequence variability (V) in both the H and L chains, referred to as the VH and VL regions respectively. The rest of the molecule has relatively constant structure.

The sites at which the antibody binds to antigen are located in the variable domain. The anti-parallel beta-sheets in the variable domain are connected by hydrophilic amino acid loops, or beta-turns, also known as the hypervariable regions, or as the complimentarity determining region (CDR). Similarly to globular proteins, antibodies use these beta-turn regions to interact with complementary sequences with high affinity and specificity. The exposition of the separate but closely disposed CDR of the two apposed H and L chains compose the antigen-binding region of the antibody. Differing patterns of loop size and amino acid sequence diversity from one antibody to another generate antibody specificities.

Certain synthetic peptides derived from CDR sequences have been shown to possess properties which are similar to the intact antibody in that they can inhibit idiotype-antiidiotype interactions, bind specific antigens, interact with cellular receptors, and stimulate biological processes.

In a following step, a peptide corresponding to the amino acid sequence of a given CDR is synthesized. The synthetic compound is a peptide in which the linear amino acid sequence or skeleton is constrained and maintained in a cyclic shape or beta-turn conformation. The compound comprises substantially the same number and type of amino acid side chains as that of the parent antibody CDRs. Moreover, the position in three-dimensional space of the amino acid's side chains or chemical groups of the peptide compound are similar to that of the CDR of the parent antibody.

However, a functional CDR mimetope does not necessarily require cyclization. A mimetope or synthetic binding agent can also be obtained by generating random samples of molecules, such as oligonucleotides, peptides or other organic molecules, and screening such samples by affinity chromatography techniques using the corresponding binding partner. A mimetope or synthetic binding agent such as an organic peptidomimetic can also be obtained by, for example, screening libraries of synthetic compounds that are capable of inhibiting the binding of an antibody to its ligand. A mimetope or synthetic binding agent can also be obtained by, for example, rational drug design. In a rational drug design procedure, the three-dimensional structure of a compound of the present invention can be analyzed by, for example, nuclear magnetic resonance (NMR) or x-ray crystallography. The three-dimensional structure can then be used to predict structures of potential mimetopes or synthetic binding agents by, for example, computer modeling. The predicted mimetope or synthetic binding agent structures can then be produced by, for example, chemical synthesis, or recombinant DNA technology.

Peptide mimetopes from this application could be combined i.e.: 2 mimetopes or more linked together (in addition to the linking to a radionuclide, cytotoxic agent . . . ). In addition, a mimetope could result from a 'consensus sequence' deduced from the alignment of multiple CDRs of different mAb.

Naturally occurring compounds, such as those from a plant, animal, insect, bacterium, fungus or the like, with binding characteristics which imitate or mimic the binding characteristics of an antibody are also foreseeable. Such naturally occurring compounds can be obtained by, for example, screening libraries of natural compounds for compounds capable of inhibiting the binding of an antibody to its ligand or otherwise able to imitate or mimic the binding characteristics of an antibody.

The term "antibody" (Ab) is intended to mean intact antibody molecules as well as fragments, or binding regions or domains thereof (such as, for example, Fab, F(ab')2 and Fv fragments) which are capable of binding an antigen. Such fragments are typically produced by proteolytic cleavage, with enzymes such as papain or pepsin. Alternatively, antigen-binding fragments can be produced through recombinant DNA technology or through synthetic chemistry.

The term "monoclonal antibody" (mAb) is intended to mean an antibody produced by a single clone of cells or a cell line derived from a single cell that has unique antigen binding characteristics or recognizes an individual molecular target. Such antibodies are all identical and have unique amino acid sequences.

The term "epitope" is intended to mean a molecular region on the surface of an antigen capable of eliciting an immune response and of combining with the specific antibody produced by such a response.

The term "cytotoxic compound" is intended to mean a compound, or molecule which is capable of killing a cell.

The term "detectable label" is intended to mean a label effective at permitting detection of a cell or portion thereof upon binding of a molecule to which the detectable label is attached to said cell or portion thereof. Alternatively, the detectable label permits detection of a cell upon internalization of the detectable label by the cell. A detectable label includes but is not limited to a radioactive label, a fluorescent label, a nuclear magnetic resonance active label, a luminescent label, a chromophore label, a positron emitting isotope for PET scanner, chemiluminescence label, or an enzymatic label.

The term "biological sample" is intended to mean a sample obtained from an individual and includes, but is not to be limited to, any one of the following: tissue, cerebrospinal fluid, plasma, serum, saliva, blood, nasal mucosa, urine, synovial fluid, microcapillary microdialysis.

The terms "treatment", "treating" and the like are intended to mean obtaining a desired pharmacologic and/or physiologic effect, such as inhibition of cancer cell growth or induction of apoptosis of a cancer cell. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing a disease or condition (e.g., preventing cancer) from occurring in an individual who may be predisposed to the disease but has not yet been diagnosed as having it; (b) inhibiting the disease, (e.g., arresting its development); or (c) relieving the disease (e.g., reducing symptoms associated with the disease).

The terms "administering" and "administration" are intended to mean a mode of delivery including, without limitation, oral, rectal, parenteral, subcutaneous, intravenous, intramuscular, intraperitoneal, intraarterial, transdermally or via a mucus membrane. The preferred one being orally. One skilled in the art recognizes that suitable forms of oral formulation include, but are not limited to, a tablet, a pill, a capsule, a lozenge, a powder, a sustained release tablet, a liquid, a liquid suspension, a gel, a syrup, a slurry, a suspension, and the like. For example, a daily dosage can be divided into one, two or more doses in a suitable form to be administered at one, two or more times throughout a time period.

The term "therapeutically effective" is intended to mean an amount of a compound sufficient to substantially improve some symptom associated with a disease or a medical condition. For example, in the treatment of cancer, a compound which decreases, prevents, delays, suppresses, or arrests any symptom of the disease would be therapeutically effective. A therapeutically effective amount of a compound is not required to cure a disease but will provide a treatment for a disease such that the onset of the disease is delayed, hindered, or prevented, or the disease symptoms are ameliorated, or the term of the disease is changed or, for example, is less severe or recovery is accelerated in an individual.

The compounds of the present invention may be used in combination with either conventional methods of treatment and/or therapy or may be used separately from conventional methods of treatment and/or therapy.

When the compounds of this invention are administered in combination therapies with other agents, they may be administered sequentially or concurrently to an individual. Alternatively, pharmaceutical compositions according to the present invention may be comprised of a combination of a compound of the present invention, as described herein, and another therapeutic or prophylactic agent known in the art.

It will be understood that a specific "effective amount" for any particular individual will depend upon a variety of factors including the activity of the specific compound employed, the age, body weight, general health, sex, and/or diet of the individual, time of administration, route of administration, rate of excretion, drug combination and the severity of the particular disease undergoing prevention or therapy.

As used herein, "pharmaceutically acceptable carrier" includes any and all solvents (such as phosphate buffered saline buffers, water, saline), dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in therapeutic compositions is contemplated. Supplementary active ingredients can also be incorporated into the compositions.

BRIEF DESCRIPTION OF THE DRAWINGS

FIG. 1 illustrates the complete nucleotide coding sequence for human PSMA (nucleotides 262 to 2514 of GenBank™ accession number: NM_004476; SEQ ID NO: 1);

FIG. 2 illustrates the complete amino acid sequence (amino acid 1 to 750) of human PSMA (GenBank™ accession number: NP_004467; SEQ 10 NO: 2);

DETAILED DESCRIPTION OF THE INVENTION

Figure 3A:
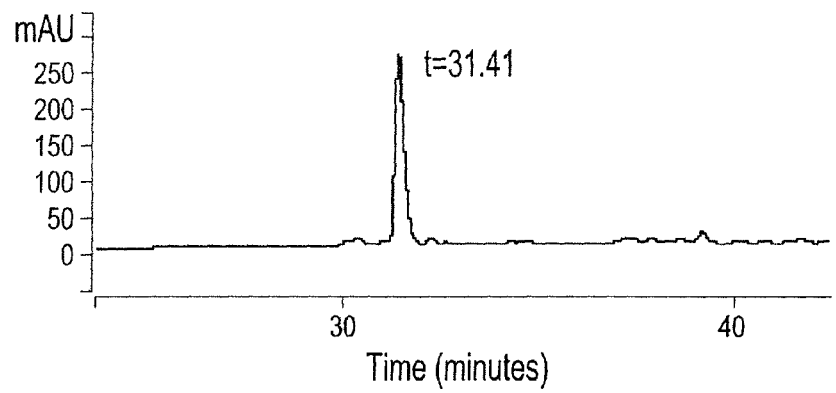
FIG. 3 illustrates the HPLC profile of a cyclic and linear form of mimetope (SEQ ID NO:24)

In accordance with the present invention there is provided mimetopes of anti-PSMA monoclonal antibodies and their use for detecting, imaging, staging, treating and monitoring of prostate cancer, and/or metastasis thereof.

In accordance with the present invention there is provided novel pharmaceutical compositions for the treatment of prostate cancer.

In accordance with the present invention there is provided a method of producing a mimetope which binds to an epitope of PSMA, comprising: determining a region of an antibody which binds to the epitope responsible for the binding; designing the mimetope based on the region; and synthesizing the mimetope.

The mimetope, or synthetic binding agent or molecule, or mixtures thereof may be unmodified or may be linked to 1) a radioimaging agent, such as those emitting radiation, for detection of the prostate cancer, and/or metastasis thereof upon binding of the antibody or binding fragment thereof, mimetope thereof, or synthetic binding agent or molecule, or mixtures thereof to the antigen, or 2) a cytotoxic agent, which kills the prostate cancer, and/or metastasis thereof upon binding of the antibody or binding fragment thereof, mimetope thereof, or synthetic binding agent or molecule, or mixtures thereof to the antigen. Alternatively, the cytotoxic agent is not toxic until internalized by the cell. Alternatively, the cytotoxic agent is toxic whether internalized or not internalized. Treatment is effected by administering the antibody or binding fragment thereof, mimetope thereof, or synthetic binding agent or molecule, or mixtures thereof to the individual under conditions which allow binding of the antibody or binding fragment thereof, mimetope thereof, or synthetic binding agent or molecule, or mixtures thereof to the antigen, and which binding results in the death of the cells of the prostate cancer, and/or metastasis thereof. In a preferred embodiment, administration is carried out on a living mammal. Such administration can be carried out orally or parenterally. In another embodiment the method is used to prevent or delay development or progression of prostate cancer, and/or metastasis thereof.

A cytotoxic agent of the present invention can be an agent emitting radiation, a cellular toxin (chemotherapeutic agent) and/or biologically active fragment thereof, and/or mixtures thereof to allow cell killing. A cytotoxic agent such as a cellular toxin and/or biologically active fragment thereof can be a synthetic product or a product of fungal, bacterial or other microorganism, such as mycoplasma, viral etc., animal, such as reptile, or plant origin. A cellular toxin and/or biologically active fragment thereof can be an enzymatically active toxin and/or fragment thereof, or can act by inhibiting or blocking an important and/or essential cellular pathway or by competing with an important and/or essential naturally occurring cellular component.

Cytotoxic agents emitting radiation for use in the present invention are exemplified by Yttrium-90 ($Y^{90}$), iodine-125 ($I^{125}$), iodine-131 ($I^{131}$) and gamma-emitting isotopes used, for example, to destroy thyroid tissue in some individuals suffering from hyperthyroidism.

Radio imaging agents emitting radiation (detectable radiolabels) for use in the present invention are exemplified by indium-111 ($In^{111}$), technitium-99 ($Tc^{99}$), or iodine-131 ($I^{131}$).

Detectable labels (non-radioactive labels) for use in the present invention can be a radioactive label, a fluorescent label, a nuclear magnetic resonance active label, a luminescent label, a chromophore label, a positron emitting isotope for PET scanner, chemiluminescence label, or an enzymatic label. Fluorescent labels are exemplified by fluorescein, and rhodamine. Chemiluminescence labels are exemplified by luciferase. Enzymatic labels are exemplified by peroxidase and phosphatase.

Cellular toxins and/or biologically active fragments thereof are exemplified by chemotherapeutic agents (anti-cancer cytotoxic compounds) known in the art, for example, cyclophosphamide and Taxol™. Biological compounds with cellular toxic effects are exemplified by saporin, *Pseudomonas exotoxin* (PE40), interferons (e.g. IFN-alpha) and certain interleukins (e.g. IL2).

In accordance with the present invention, there is provided a mimetope or synthetic binding agent or molecule which binds to an extracellular region of PSMA.

In accordance with the present invention, there is provided a mimetope or synthetic binding agent or molecule which binds to an extracellular region of PSMA, ranging between amino acid 51 to amino acid 67, amino acid 85 to amino acid 102, amino acid 104 to amino acid 118, amino acid 161 to amino acid 173, amino acid 236 to amino acid 245, amino acid 278 to amino acid 288, amino acid 345 to amino acid 354, amino acid 490 to amino acid 500, amino acid 531 to amino acid 545, amino acid 551 to amino acid 567, amino acid 608 to amino acid 619, amino acid 649 to amino acid 660, amino acid 716 to amino acid 724, or amino acid 738 to amino acid 750 which regions comprise an amino acid sequence selected from the group consisting of SEQ ID NOs: 3-16, respectively.

A mimetope which binds to another epitope of PSMA and a mimetope which binds to an epitope of another prostate cancer antigen is also encompassed by the present invention.

Mimetopes offer several advantages over "natural" antibodies. Mimetopes imitate or mimic the antigen binding biological activity of antibodies. Mimetopes offer advantages over antibodies as they are small and more resistant to protease degradation because of their cyclic nature. As they are of small molecular weight, they are more likely to be able to penetrate target tissue, and are not effective immunogenic targets for the body's immune system. These factors confer biostability for mimetopes in vivo, and allow them to penetrate target organs and cells. These characteristics make them highly suitable as replacements for natural antibodies in both detection, imaging and diagnostic protocols for the localization and/or staging of prostate cancer, and/or metastasis thereof and therapeutic options to treat prostate cancer, and/or metastasis thereof.

Furthermore, since mimetopes are synthetic compounds, they can be easily modified physically and chemically to perform specific functions. One such modification is to tag the mimetope molecule with a radioactive isotope which emits gamma radiation. Radioactive signals emitted by the tagged mimetopes are concentrated in cancerous masses, particularly metastatic lesions, and allow clinicians to produce an image of localized cancer. This provides the investigator with information regarding the size, location, stage and extent of prostate cancer, and/or metastasis thereof and allows for the detection of the spread of cancer to surrounding tissues or organs. The ability to localize cancer provides clinicians with valuable information useful for staging a malignancy and determining a course of treatment for the individual.

Mimetopes also offer great potential for prostate cancer therapy as they can be easily linked to therapeutic agents and facilitate drug delivery directly to the prostate gland.

Mimetopes also offer other great benefits. The fact that mimetopes are specifically designed and characterized means that their binding region is much more precisely defined than, for example, an entire anti-PSMA antibody. In addition in, for example, a competitive assay, the use of a mimetope rather than, for example, a whole anti-PSMA antibody, offers greater precision.

Regardless of whether the antibody or binding fragment thereof, mimetope thereof, or mixtures thereof of the present invention is used for treatment, detection, or imaging, it can be administered orally, parenterally, subcutaneously, intravenously, intramuscularly, intraperitoneally, by intranasal instillation, by intracavitary or intravesical instillation, intraocularly, intraarterially, intralesionally, as an aerosol, or by application to mucous membranes, such as, that of the nose, throat, and bronchial tubes. It may be administered alone or with a pharmaceutically or physiologically acceptable carrier, excipient, or stabilizer, and can be in solid or liquid form such as, tablet, capsule, powder, solution, suspension or emulsion.

The treatment and/or therapeutic use of the mimetope, antibody or binding portion thereof or synthetic binding peptide or molecule of the present invention can be used in conjunction with other treatment and/or therapeutic methods. Such other treatment and/or therapeutic methods include surgery, radiation, cryosurgery, thermotherapy, hormone treatment, chemotherapy, vaccines, other immunotherapies, and other treatment and/or therapeutic methods which are regularly described.

In addition to methods of treatment and/or therapeutic use, the antibodies and/or mimetopes of the present invention, by their binding positions on the PSMA protein, can be used for epitope mapping of the architecture of the PSMA protein in epitope mapping studies. The antibodies and/or mimetopes of the present invention can also be used as probes for screening a library of molecules, agents, proteins, peptides and/or chemicals to identify a molecule, agent, protein, peptide and/or chemical able to bind to the mimetope. Such a library could be a chemical library, antibody library, phage display library, peptide library or library of natural compounds. The identified molecule, agent, protein, peptide and/or chemical could be an antagonist or agonist of PSMA.

The present invention will be more readily understood by referring to the following examples which are given to illustrate the invention rather than to limit its scope.

Example 1

Peptide Synthesis and Cyclisation

Example 1 relates to the synthesis and cyclisation of peptide mimetopes binding to PSMA, an extracellular region of PSMA or peptides thereof.

In order to improve the therapeutic efficacy of the peptidic compounds of the present invention, several modifications of the peptide were made by substituting one amino acid with a related amino acid. Substitution of the amino acids of the mimetope of the present invention includes, but are not limited to a variant wherein at least one amino acid residue in the polypeptide has been replaced by a different amino acid, either related by structure or by side chain functionality.

Such substitutions are preferably made in accordance with the following description of relations among amino acids

TABLE 2

Relations among amino acids

Small aliphatic, non polar or slightly polar: Ala, Ser, Thr, Met, Leu, Ile, Val, *(Pro, Gly)
Large aliphatic, non polar: Met, Leu, Ile, Val, *(Cys)
Polar, negatively charged and their amides: Asp, Asn, Glu, Gln TABLE 2-continued Relations among amino acids Polar, positively charged: His, Arg, Lys
Large aromatic: Phe, Tyr, Trp

*The three amino acid residues placed between parenthesis play a special role in protein architecture. 'Gly' is the only residue lacking a side chain and thus imparts flexibility to the chain. This however tends to promote the formation of a secondary structure other than the alpha-helical structure. 'Pro', because of its geometry, tightly constrains the chain. 'Cys', is capable of participating in disulfide bond formation.

As an example, the residue 'Tyr' is related to the group of large aromatic amino acids such as Phe and Trp. Because of this hydrogen bonding potential, it also has kindship with 'Ser' and 'Thr'. Table 3 cites examples of potential substitution of every natural amino acids.

TABLE 3

Substitution of amino acids

| Residue | Substitution |
| --- | --- |
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |
| Pro | Ala, Gly |

Any amino acid component of the mimetope of the present invention can be substituted by its corresponding enantiomer (the same amino acid but of opposite chirality). Therefore, any amino acid naturally occurring in the L-configuration may be substituted by its corresponding enantiomer, that is, an amino acid having the D-configuration. Amino acids of the L-configuration have the same chemical structural type as the amino acids of the D-configuration, but have opposite chirality. The L- and D-configuration can also generally be referred to as R- or the S-configuration. Additional variations include β- and γ-amino acids, providing for a different spatial arrangement of chemical groups.

In addition to the substitutions outlined above, synthetic amino acids providing similar side chain functionality can also be introduced into the peptide. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, iso-butyl, and iso-pentyl.

Non-carboxylate amino acids can be made to possess a negative charge, as provided by phosphono- or sulfated (e.g. —$SO_3H$) amino acids, which are to be considered as non-limiting examples.

Other substitutions may include unnatural alkylated amino acids, made by combining an alkyl group with any natural amino acid. Basic natural amino acids such as lysine and arginine may be substituted with alkyl groups at the amine ($NH_2$) functionality. Yet other substitutions include nitrile derivatives (e.g., containing a CN-moiety in place of the $CONH_2$ functionality) of asparagine or glutamine, and sulfoxide derivative of methionine. In addition, any amide linkage in the peptide may be replaced by a ketomethylene, hydroxyethyl, ethyl/reduced amide, thioamide or reversed amide moieties.

Covalent modifications of the peptides are thus included within the scope of the present invention. Such modifications may be introduced into the mimetope by reacting targeted amino acid residues of the polypeptide with an organic derivatizing agent capable of reacting with selected side chains or terminal residues of the polypeptide. The following examples of chemical derivatives are provided by way of illustration only, and are not meant to limit the scope of the present invention. Cysteinyl residues may be reacted with alpha-haloacetates (and corresponding amines), such as 2-chloroacetic acid or chloroacetamide, to provide carboxymethyl or carboxyamidomethyl derivatives. Histidyl residues may be derivatized by reaction with compounds such as diethylpyrocarbonate (e.g., at pH 5.5-7.0) because this reagent is relatively specific for the histidyl side chain. p-Bromophenacyl bromide may also be used (e.g., where the reaction is preferably performed in 0.1 M sodium cacodylate at pH 6.0). Lysinyl and amino terminal residues may be reacted with compounds such as succinic or other carboxylic acid anhydrides. Other suitable reagents for derivatizing (x-amino-containing residues include compounds such as imidoesters (e.g. methyl picolinimidate); pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, such as phenylglyoxal, 2,3-butanedione, 1,2-cyclohexanedione, and ninhydrin, according to known method steps. The derivatization of arginine residues requires that the reaction be performed under alkaline conditions, because of the high pKa of the guanidine functional group. Furthermore, these reagents may also react with the amine groups of lysine, as well as with the arginine ε-amino group.

The specific modification of tyrosinyl residues per se is well-known. Specific and non-limiting examples include the introduction of spectral labels onto tyrosinyl residues by reaction with aromatic diazonium compounds or tetranitromethane. N-acetylimidazol and tetranitromethane may be used to form O-acetyl tyrosinyl species and 3-nitro derivatives, respectively.

Carboxyl side groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions. Glutaminyl and asparaginyl residues may be deamidated to the corresponding glutamyl and aspartyl residues.

Other modifications of the mimetopes of the present invention may include hydroxylation of proline and lysine; phosphorylation of the hydroxyl group of seryl or threonyl residues; methylation of the alpha-amino group of lysine, arginine, and histidine; acetylation of the N-terminal amine; methylation of main chain amide residues (or substitution with N-methyl amino acids) and, in some instances, amidation of the C-terminal carboxyl groups, according to methods known in the art.

The above description of possible modifications of a peptide should not be considered as a limitation to the scope of the approaches, nor should it be considered as a limitation to the possible modifications that can be engineered using the mimetope of the present invention. Due to the complex nature of the peptide folding, neither the structure nor the biological effect of the modification can be predicted with absolute certainty. Those skilled in the art will readily appreciate that the modified peptides should be tested in bioassays as described in the present invention in order to confirm biological activity.

Table 4 shows the sequence of amino acids of the peptide mimetopes.

TABLE 4

| | |
|---|---|
| LysGluSerTyrAsnPheIleThr | (SEQ ID NO: 17) |
| GlyGlyPheProTyrGly | (SEQ ID NO: 18) |
| GlyPheProTyrGlyGly | (SEQ ID NO: 19) |
| LeuGlyArgProPheAlaHis | (SEQ ID NO: 20) |
| LeuGlyArgGlyPheAlaHis | (SEQ ID NO: 21) |
| GlyGlyArgProPheGlyGly | (SEQ ID NO: 22) |
| GlyGluAspTyrTyrThrSerArgTyrGlyPhePheAspVal | (SEQ ID NO: 23) |
| CysLysGluSerTyrAsnPheIleThrCys | (SEQ ID NO: 24) |
| CysGlyGlyPheProTyrGlyCys | (SEQ ID NO: 25) |
| CysGlyPheProTyrGlyGlyCys | (SEQ ID NO: 26) |
| CysLeuGlyArgProPheAlaHisCys | (SEQ ID NO: 27) |
| CysLeuGlyArgGlyPheAlaHisCys | (SEQ ID NO: 28) |
| CysGlyGlyArgProPheGlyGlyCys | (SEQ ID NO: 29) |
| CysGlyGluAspTyrTyrThrSerArgTyrGlyPhePheAspValCys | (SEQ ID NO: 30) |
| CysGlyGlyPheProTyrGlyCysTyr | (SEQ ID NO: 31) |
| CysGlyPheProTyrGlyGlyCysTyr | (SEQ ID NO: 32) |
| CysLeuGlyArgProPheAlaHisCysTyr | (SEQ ID NO: 33) |
| CysLeuGlyArgGlyPheAlaHisCysTyr | (SEQ ID NO: 34) |
| CysGlyGlyArgProPheGlyGlyCysTyr | (SEQ ID NO: 35) |

Each peptides are synthesized by solid F-MOC chemistry to greater than 95% purity. Peptides were designed with and without additional cysteine residues at their N-terminus and C-terminus to allow for cyclisation.

One strategy to fold a linear peptide into a cyclic, constrained entity involves, for example, the addition of 2 cysteines at least 4 residues apart from each other within the sequence of the peptide (such as in: Williams et al 1991 JBC 266:5182). The formation of an intra-peptide disulfide bridge by cysteines oxidation results in a peptide with a cyclic conformation. To allow the formation of a disulfide bridge, the lyophilized peptide is dissolve in water at low concentration (2 mg/ml) and gently agitated under ambient air for 24 hours or more. The oxidation of free cysteine into cystine can be monitored over time by an Ellman test (Habeeb A F, Anal. Biochem 56, 60-65, 1973).

Figure 3B:
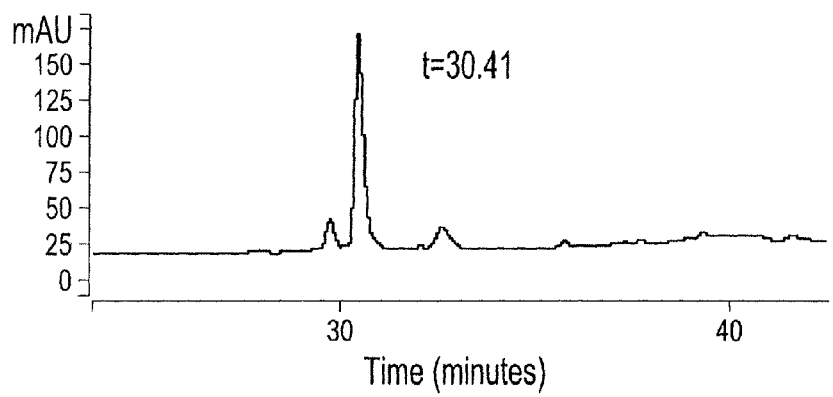
Figure 3C:
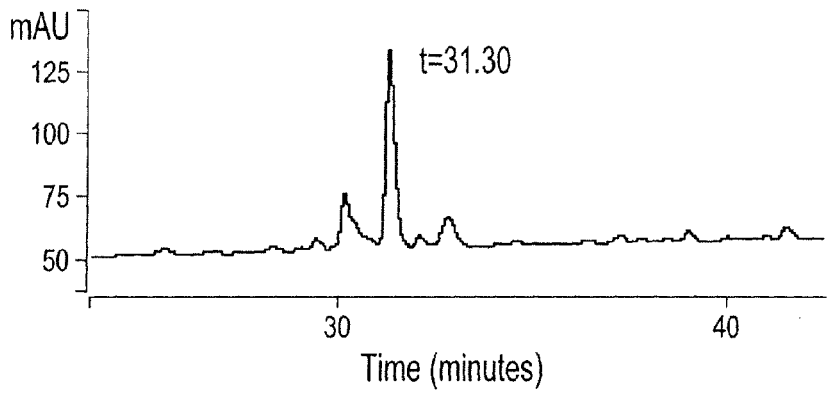

The transformation of a linear peptide into a cyclic form can be observed by HPLC analysis and further assessed by mass spectroscopy. A sample of the peptide in water is withdrawn at the initial time of solubilsation and at regular intervals over 3-4 days. The samples are analyzed by reverse-phase HPLC over a C18 column. A time dependent shift in the retention time of the sample is indicative that a change in the structure of the peptide occurs, such as cyclisation. FIG. 3 A, B shows the HPLC profile of an oxidized sample at t=0 and 120 h. The peak of the oxidized sample eluted 1 minute earlier than the peak observed at initial solubilization time as a consequence of the peptide oxidation. Upon reduction of the oxidized sample by treatment with 250 mM DTT (FIG. 3C), the sample's retention time returned to that of the initial value (i.e. reduced and linear form). The oxidation of cysteine-containing peptides could result in the formation of peptide dimer and oligomer, in addition to cyclic monomer of peptide. To obtain homogenous cyclic monomers, the oxidized peptide solution is purified by HPLC using a. C18 column. Fractions containing the oxidixed peptide monomers are collected and lyophilized.

The oxido-reduction state of the sample can be accurately determined by measuring the molecular weight of the sample by mass spectrometry. The oxydation of two cysteines upon formation of a cystine bridge is accompanied by the loss of 2 protons. Table 5 compares the molecular weight of oxidized and reduced peptide SEQ ID NO.:24). The values of the samples measured are not different from the theoretical molecular weight of the oxidized and reduced peptide.

TABLE 5

Theorical and experimental molecular weight of mimetope (SEQ ID NO: 24) linear and cyclized

| Sample | Theorical molecular weight (Da) | Experimental molecular weight (Da) |
|---|---|---|
| SEQ ID NO: 24 linear | 1206.4 | 1206.2 |
| SEQ ID NO: 24 cyclized | 1204.4 | 1204.2 |

Example 2

Identification of Mimetope Binding to PSMA

Potential mimetopes were synthesized and cyclized as described in Example 1. A 96 wells plate was then coated with the mimetope, or an unrelated peptide (neg. ctrl.) by filling the wells with 100 ul of a solution of increasing concentrations of mimetope in water, in the presence of the absence of 0.5 mM DTT, and allowed to dry overnight. The presence of DTT in the coating solution allows the reduction of the mimetope's oxidized cysteines and promotes the linear form of the peptide versus the cyclic form. The wells are then blocked with casein 3% in TBST for 1 hour, then washed with TBST. A solution of $^{125}$I-PSMA (5 uCi/pmol) at 5 nM was then applied to the wells and incubated for 4 hours at 4° C. The wells were quickly rinsed 3 times with TBST and the bound radioactivity counted in a gamma counter.

Figure 4:
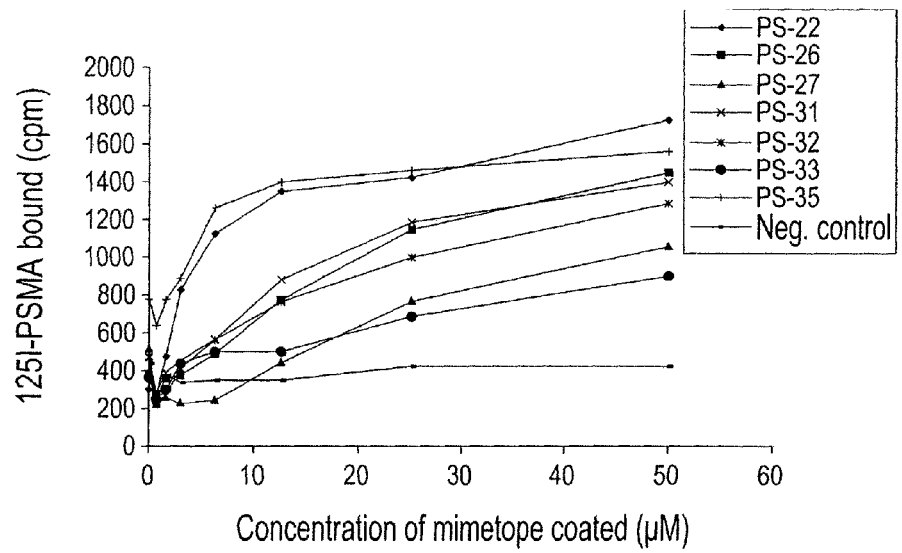
FIG. 4 illustrates the binding of $^{125}$I-PSMA to cyclic mimetopes.
Figure 5:
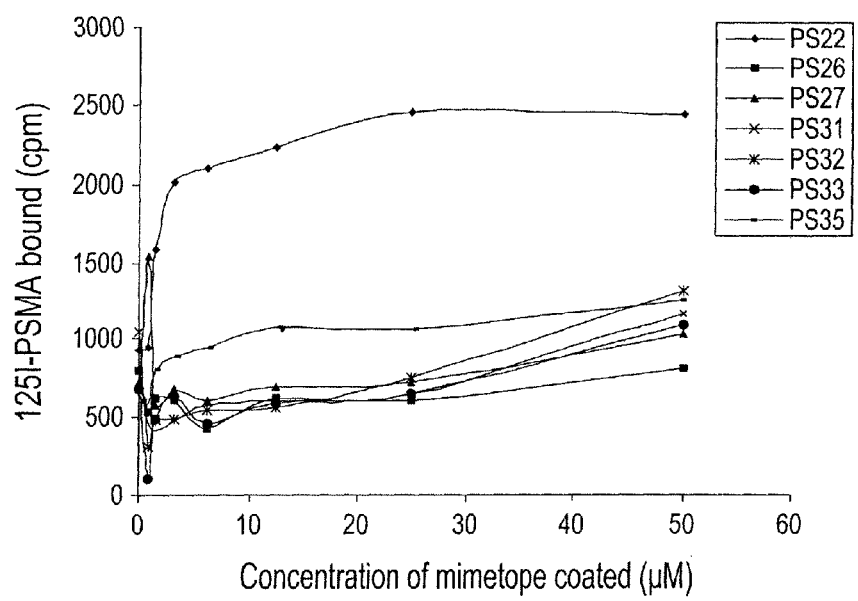
FIG. 5 illustrates the binding of $^{125}$I-PSMA to linear mimetopes.

FIGS. 4 and 5 show the binding of $^{125}$I-PSMA to various cyclized or linear mimetopes, respectively. The binding of $^{125}$I-PSMA to most of the mimetope was greatly reduced when coated in their linear form, except for mimetope SEQ ID NO:24), which retained a comparable PSMA binding potential in either oxidized or reduced state.

Example 3

Use of Mimetopes for the Detection/Diagnostic of Prostate Cancer

Example 3 relates to the use of mimetopes of the present invention for the detection/diagnosis of prostate cancer and/or metastases thereof.

The present invention provides a ligand, which recognize and bind specifically to an extracellular epitope of PSMA. The ligand can be used as a vehicle to target another substance to sites where PSMA is expressed, such as in prostate cancer or metastatic prostate cancer. Such a substance could be effective at detecting PSMA expressing cells by radio-scintigraphy, for example, upon proper conditions permitting binding of the ligand complex in vivo. Vehicle-coupled radionuclide such as In$^{111}$, or Tc$^{99}$ is currently used in clinics, or under investigation, as contrasting agent for such an application.

Example 4

Use of Mimetopes for the Treatment of Individuals with Prostate Cancer

Example 4 relates to the use of mimetopes of the present invention for the treatment of individuals with prostate cancer and/or metastases thereof.

As a specific targeting agent, the anti-PSMA mimetope could be used to deliver a killing agent to the cells upon binding to it. Cell toxic agent such as chemotherapeutic agent, biological toxins, or strong gamma emitting radionuclides such as Y$^{90}$ or I$^{125}$ are currently used in clinics, or under investigation for therapeutic usage. The cell bound mimetope conjugate could also be internalised by the cell and thus permit the use of intracellularly acting cytotoxic agents.

Example 5

Analysis of the Interaction Between PSMA and Mimetope (SEQ ID NO:24) by Surface Plasmon Resonance (SPR)

An estimation of the affinity of various candidate mimetopes for PSMA can be obtained by various ligand-binding methods such as surface plasmon resonance.

The experiments were carried out at 25° C. on a Biacore™ 3000 optical biosensor (Biacore Inc., Piscataway, N.J.). The data collection rate was set to 10 Hz for every assay. Phosphate-buffered saline (PBS) buffer containing 0.005% Tween™ 20 was used as running buffer for SPR experiments as well as to dilute the injected protein (PSMA). The mimetope (SEQ ID NO:24) peptide (13 uM, in 10 mM acetic acid, pH 4.0) was covalently immobilized onto CM5 biosensor chips using standard amine coupling chemistry (between 150 and 300 RUs). A separate flow cell was similarly activated and blocked to be used as control.

Kinetic experiments were carried out in duplicate at a flow rate of 20 uL/min. The interaction between PSMA with the mimetope peptide of SEQ ID NO:24 was monitored as follows: concentrations of PSMA (3.5 to 120 nM), in addition to buffer (4 different injections) were randomly injected in duplicate for 540 s., followed a 1000-s buffer injection over both mimetope (SEQ ID NO:24) peptide and mock surfaces. Surface regeneration between each PSMA injection was performed with a 30-s pulse of 25 mM NaOH solution (20 uL/min) followed by an EXTRACLEAN and a WASH IFC procedures (Biacore Instrument Handbook). Before any data collection, the mimetope (SEQ ID NO:24) and mock surfaces were conditioned by 5 consecutive regeneration protocols as described above in order to increase reproducibility.

The data preparation was done as described elsewhere by the method of double referencing (Rich, R. L. and Myszka, D. G. (2000) Curr. Opin. Biotechnol. 11, 54-61). All the corrected sensorgrams were reduced to 500 evenly spaced sampling points. Global analysis of the set of sensorgrams was performed using a simple Langmuirian kinetic model available in SPRevolution software package.

Figure 6A:
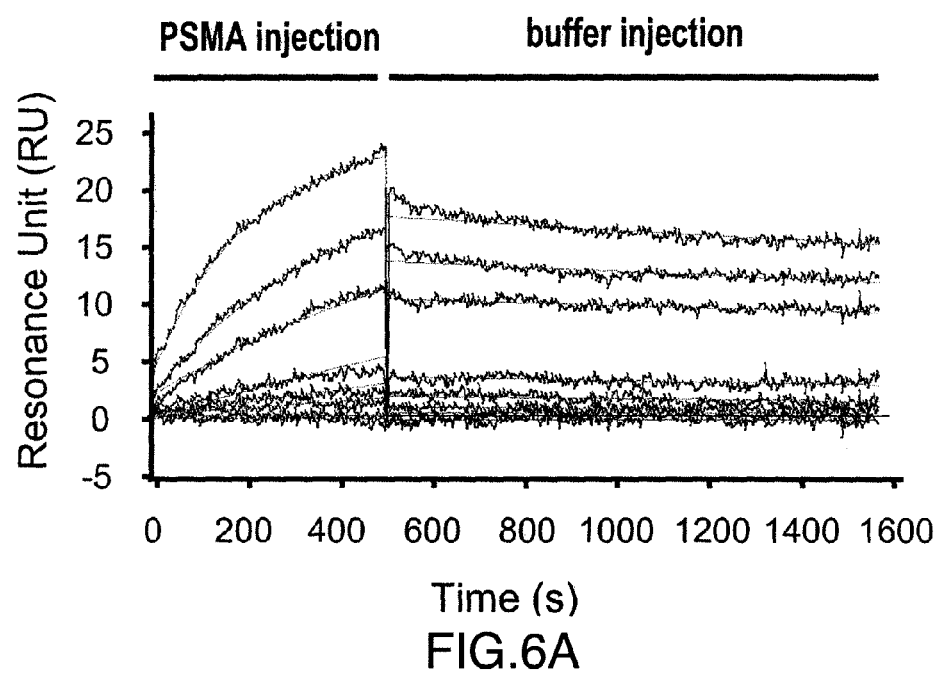
FIG. 6 illustrates the affinity and kinetic constant of PSMA for mimetope (SEQ ID NO: 24) by surface plasmon resonance.
Figure 6B:
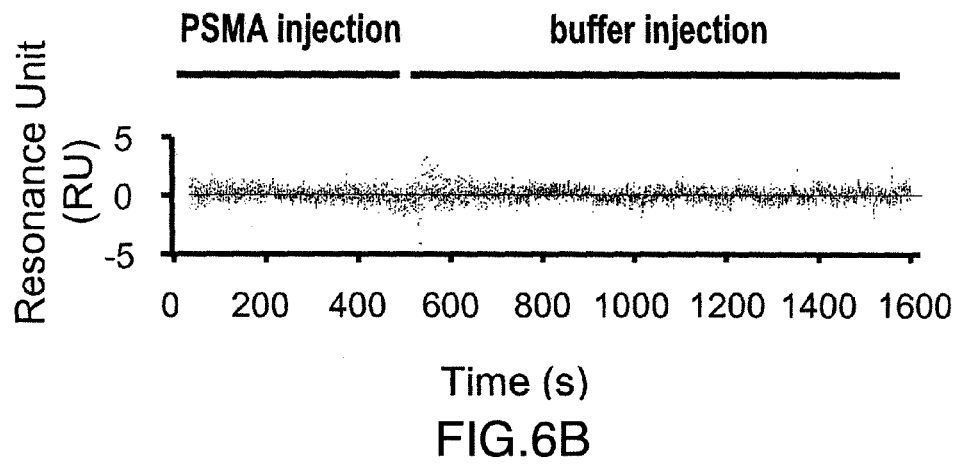

PSMA interactions with mimetope (SEQ ID NO:24) interactions were followed in real-time with a Surface Plasmon Resonance (SPR)-based Biosensor. Injections of PSMA over a mimetope (SEQ ID NO:24) immobilized surface and over a mock surface clearly indicated that the interactions between mimetope (SEQ ID NO:24) and PSMA were specific. That is, we observed a higher response in Resonance Units (RUs) when PSMA was injected over the mimetope (SEQ ID NO:24) surface as compared to the control one. Typical control-corrected sensorgrams corresponding to the interactions of PSMA (injected at various concentrations) with mimetope (SEQ ID NO:24) are shown in FIG. 6. Global analysis of these interactions allowed for the determination of the apparent association and dissociation rates of the interaction as well as the apparent thermodynamic dissociation constant. Those are $k_{on}=(36.4+/-2)\times 10^3$ M$^{-1}$ s$^{-1}$ and $k_{off}=(1.2+/-0.1)\times 10^{-4}$ s$^{-1}$; $K_d=3.3+/-0.4$ nM.

Example 6

Evaluation of the Reactivity of the Mimetope by Dot Blot

The specificity of the mimetope (SEQ ID NO:24) can be evaluated on various substrate by dot blot. A piece of PVDF membrane was spotted with a volume of about 5 ul of purified recombinant PSMA (1 ug), BSA (1 ug), PSMA-expressing LNCaP cells homogenate (3 ug), and PSMA-deficient PC-3 cells homogenate (3 ug). The proteins were allowed to dry under ambient air before the membrane is successively blocked by soaking in solutions of i) 3% casein in TBST; 1 hour, ii) avidin and biotin (Dako Cytomation; biotin blocking system, according to the manufacturer's recommendation), and iii) 3% hydrogen peroxide in water (30 minutes). The membrane is then washed and soaked into a solution of the biotinylated mimetope (SEQ ID NO:24) at concentration of 25 uM in TBST, and allowed to incubate in a humidified chamber at 4° C. for 12 hours. Mimetope (SEQ ID NO: 24) was synthesized with an additional biotin-Tyr at its amino terminal to allow it to be detected using a commercial streptavidin-horseradish peroxidase amplification system (Vector Laboratories; Vectastain™ Elite ABC kit, according to the manufacturer's recommendation). The reactivity of the mimetope is revealed by chemiluminescence (Pierce; SuperSignal™ west pico chemiluminescence substrate, according to the manufacturer's recommendation).

Figure 7:
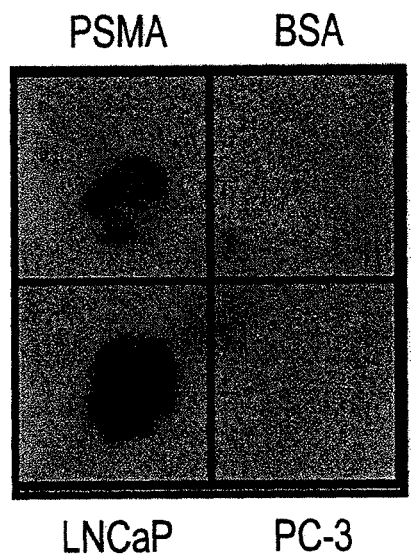
FIG. 7 illustrates the reactivity of a biotinylated mimetope (SEQ ID NO:24) by dot blot on human prostate cancer cells.
Figure 8A:
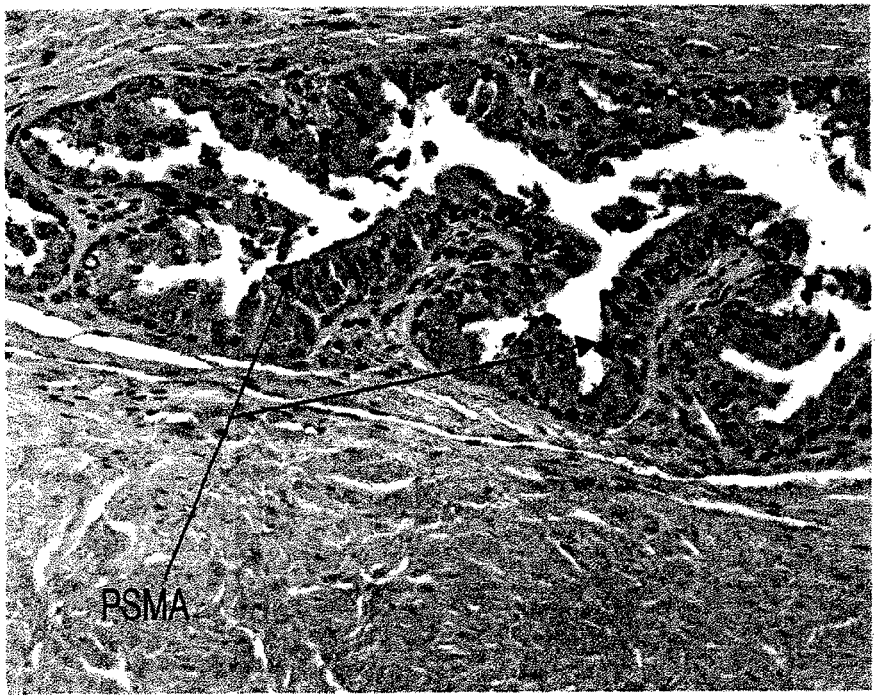
FIG. 8 illustrates the reactivity of a biotinylated mimetope (SEQ ID NO:24) by immunohistochemistry.
Figure 8B:
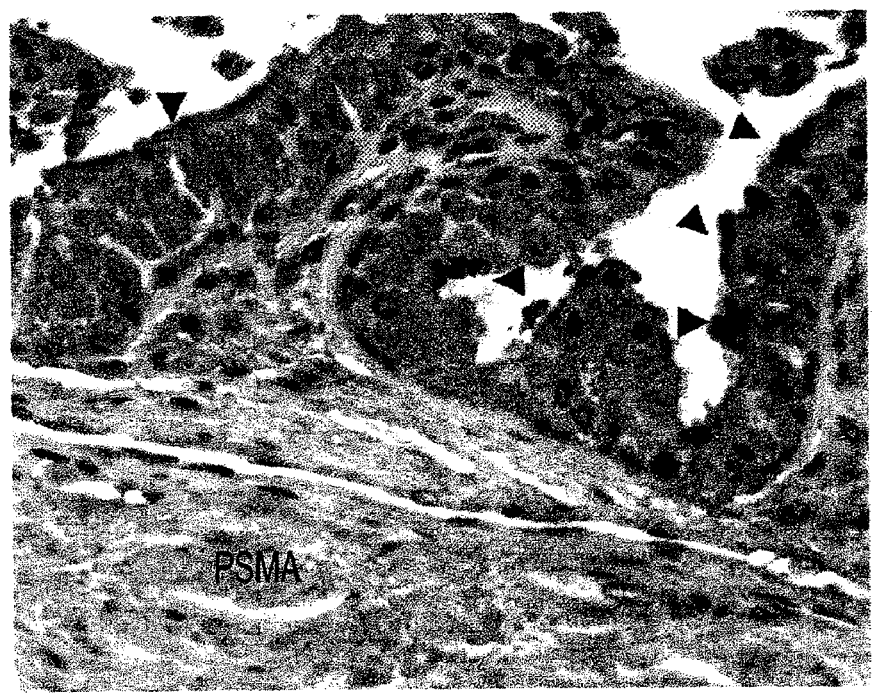
Figure 8C:
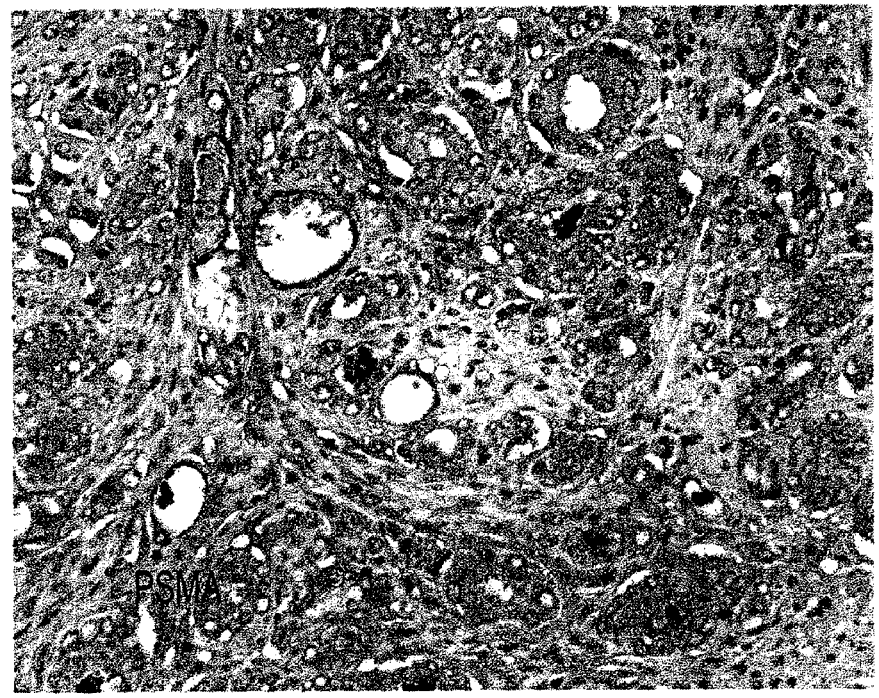
Figure 8D:
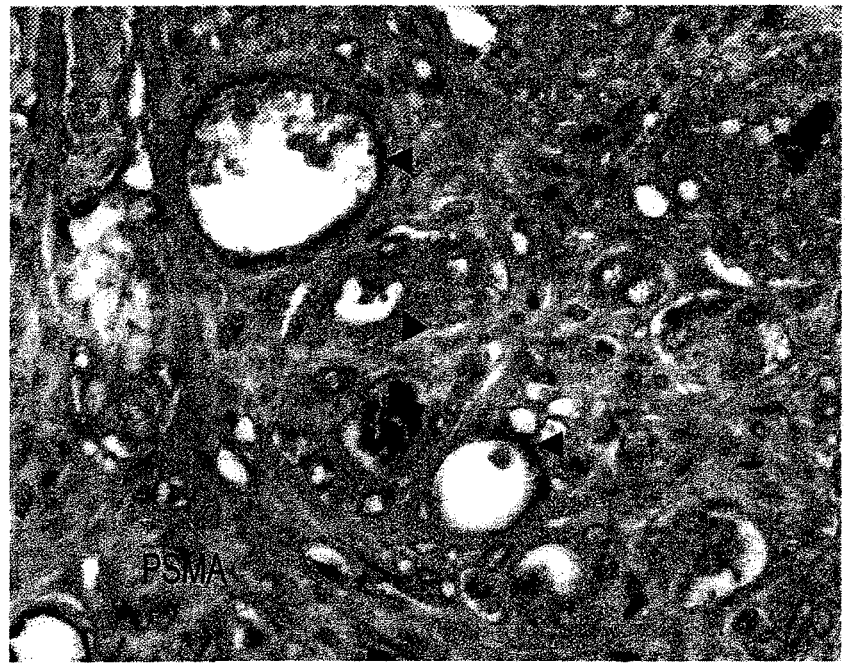
Figure 8E:
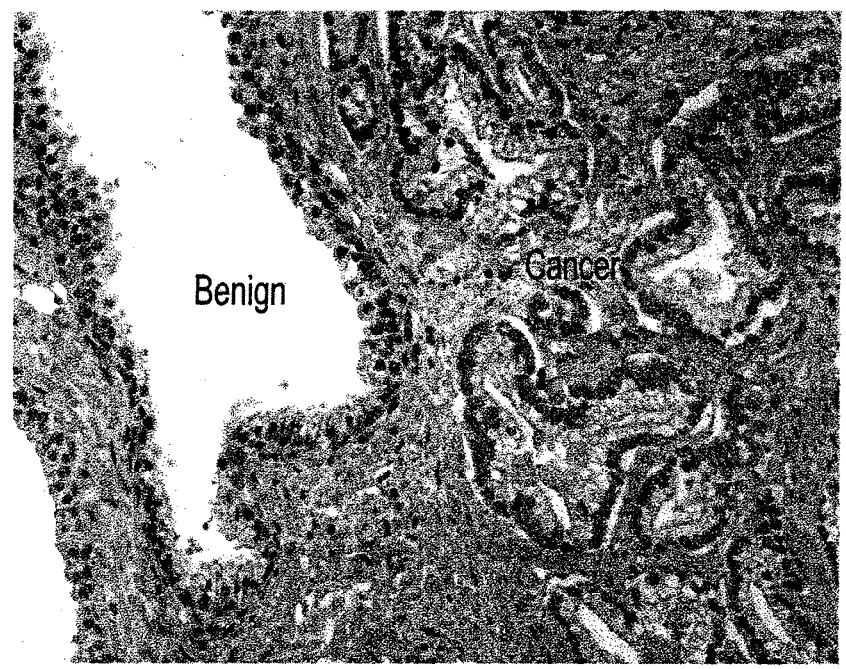

FIG. 7 shows that the mimetope (SEQ ID NO:24) positively reacts with PSMA and LNCaP cells lysate. However, no reactivity was detected on BSA or PC-3 cells.

Example 7

Evaluation of the Reactivity of the Mimetope by Immunohistochemistry

Another way to assess the specificity of the mimetope is to evaluate its reactivity on human prostate cancer tissue by immunohistochemistry. Parafin-embedded human prostate tissue slides were deparafinized by soaking in 2 baths of xylene for 5 min. and then rehydrated stepwise by soaking in baths of ethanol ranging from 100, 95, 90, 75 and 50%, and then lastly in PBS. Prior to reactivity with the mimetope, the tissue is heat treated in a basic antigen retrieval solution according to manufacturer's recommendation (LabVision). Blocking of endogenous peroxidase, proteins, biotin and streptavidin binding sites is then performed successively to reduce non-specific background to the maximum as it is done usually in the art. The tissue is then flooded with a solution containing or not a biotinylated mimetope (SEQ ID NO:24) at concentration of 100 uM in TBST, and allowed to incubate in a humidified chamber at 4° C. for 12 hours. Mimetope (SEQ ID NO:24) was synthesized with an additional biotin-Tyr at its amino terminal to allow it to be detected using a commercial streptavidin-horseradish peroxidase amplification system (Dako, catalysed amplification system). The reactivity and the specificity of the mimetope is evaluated by examination of the tissue slide under a light microscope.

FIG. 8 shows mimetope staining of prostatic tissue. In benign prostatic tissue (A, B), the staining is localized to prostatic acinar cells, and more specifically to the apical/luminal aspect of prostate acinar cells. A similar reactivity pattern is also found in moderate to poorly differentiated prostatic adenocarcinoma (C, D). The specificity of the reactivity of the mimetope can be appreciated by the absence of immunoreactivity in prostatic basal cells and surrounding prostatic stroma. The negative control (minus mimetope), shows complete absence of immunostaining in benign and malignant prostatic glands as well as stroma (E).

Example 8

Identification of Aminoacids of Mimetope Involved in Binding to PSMA

The aminoacids of a mimetope required for the binding to PSMA can be identified by a method known as alanine scan. By this method, a given mimetope is synthesized in multiple version in which the aminoacids at each position is replaced successively with a neutral residue, such as an alanine. Each alanine-mimetope generated is then tested for binding to PSMA as described. A residue important for the binding of the mimetope to PSMA can be identified as such by the reduced binding of the corresponding alanine-mimetope.

As an example, an alanine scan was performed on mimetopes (SEQ ID NO:24). Table 6 shows the original amino acid sequence of mimetope (SEQ ID NO:24) and the derived alanine-mimetope (SEQ ID NO:36 to 43).

TABLE 6

Alanine-mimetope derived from SEQ ID NO: 24

| Reference | Sequence | SEQ ID NO: |
|---|---|---|
| ps 63 | CysAlaGlnSerTyrAsnPheIleThrCys | 36 |
| ps 64 | CysLysAlaSerTyrAsnPheIleThrCys | 37 |
| ps 65 | CysLysGlnAlaTyrAsnPheIleThrCys | 38 |
| ps 66 | CysLysGlnSerAlaAsnPheIleThrCys | 39 |
| ps 67 | CysLysGlnSerTyrAlaPheIleThrCys | 40 |
| ps 68 | CysLysGlnSerTyrAsnAlaIleThrCys | 41 |
| ps 69 | CysLysGlnSerTyrAsnPheAlaThrCys | 42 |
| ps 70 | CysLysGlnSerTyrAsnPheIleAlaCys | 43 |

An estimation of the affinity of various alanine-mimetopes for PSMA can be obtained by a radioligand-binding assay (Lee E. Limbird, Cell Surface Receptors, A short course on theory and methods, third Ed, 2005. Springer, N.Y., USA). A competitive binding experiment measures the binding of a single concentration of labeled ligand to a receptor molecule in the presence of various concentration of another unlabeled ligand. The concentration of unlabeled drug that reduces radioligand binding by 50% is the inhibitory concentration 50%, or IC50.

For a typical competition binding experiment, the mimetope is coated to a solid support such as a 96-well plate by allowing 100 ul of a 10 uM solution of the mimetope (SEQ ID NO:24) in water to dry in the wells. The wells are then washed with TBST and blocked with 3% casein in TBST to minimize non-specific binding. The wells are then incubated with 1 nM $^{125}$I-PSMA at a specific activity of about 80 000 dpm/pmol, containing 0 or 10 uM of alanine-mimetope. The plate is incubated O/N at 4° C. then the wells are rapidly washed with TBST to remove the unbound ligand fraction, and then counted in a gamma counter. The radioactivity counted in each wells represents the bound fraction of the ligand. An alanine-mimetope that binds to PSMA will thus reduce the binding of $^{125}$I-PSMA to the coated (SEQ ID NO:24).

Figure 9:
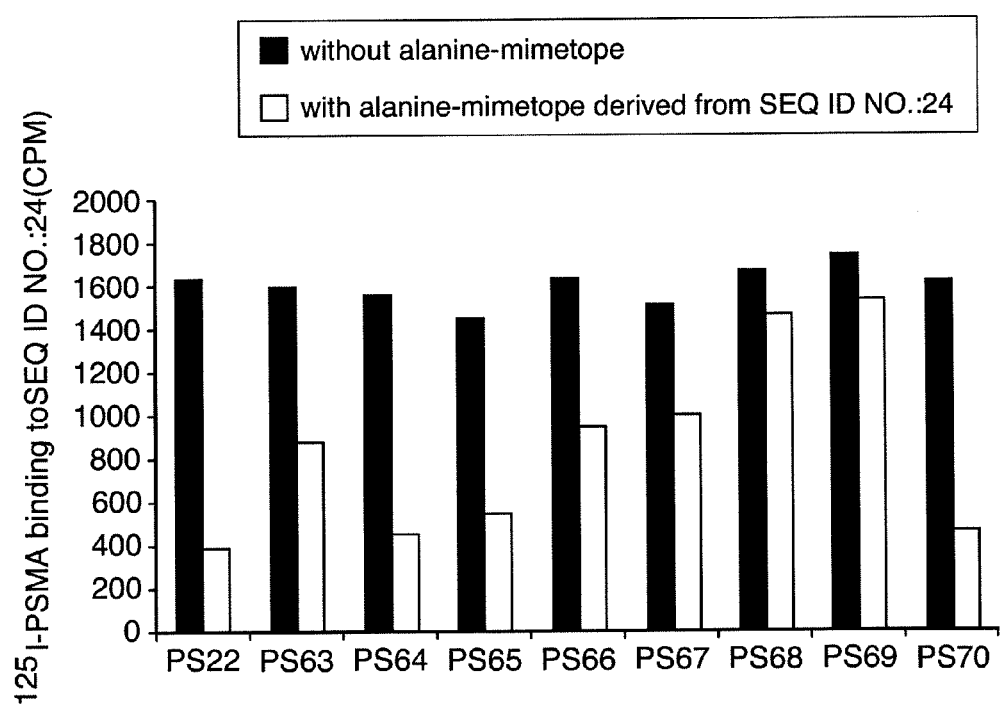
FIG. 9, shows results of competition between SEQ ID NO.:24 and alanine-mimetopes derived from SEQ ID NO.:24 for binding to $^{12}$I-labeled PSMA. Black bars represent the radioactivity measured following binding of $^{125}$I-PSMA to the coated mimetope (SEQ ID NO.:24) in absence of alanine-mimetope derived from SEQ ID NO.:24. White bars represent the radioactivity measured following binding of $^{125}$I-PSMA to the coated mimetope (SEQ ID NO.:24) in the presence of PS22 or in the presence of each of the alanine-mimetope derived from SEQ ID NO.:24 (PS63, PS64, PS65, PS66, PS67, PS68 PS69 and PS70).

FIG. 9 shows the results of the competition of each alanine-mimetopes (SEQ ID NO:36 to 43) for the binding between $^{125}$I-PSMA and mimetope (SEQ ID NO:24). In FIG. 9, the black bars represent the radioactivity measured following binding of $^{125}$I-PSMA to the coated mimetope (SEQ ID NO.: 24) without any alanine-mimetope derived from SEQ ID NO.:24, the white bars represent the radioactivity measured following binding of $^{125}$I-PSMA to the coated mimetope (SEQ ID NO.:24) in the presence of PS22 or in the presence of each of the alanine-mimetope derived from SEQ ID NO.: 24 (PS63, PS64, PS65, PS66, PS67, PS68, PS69 and PS70). By this method, we identified that residue #6 or 7 (excluding Cys) are necessary for the binding of mimetope (SEQ ID NO:24) to PSMA because they reduce significantly the binding of $^{125}$I-PSMA to mimetope (SEQ ID NO:24). Residues #1, #4 and #5 are moderately involved in PSMA binding to mimetope (SEQ ID NO:24) and residues #2, #3 and #8 have minimal role on the binding.

The results obtained from the alanine scan can help in improving the binding properties of the mimetope. An aminoacid identified as important in the binding can be replaced by an aminoacid of similar biochemical property. For example, a leucine can be replaced with another hydrophobic aminoacid such as a valine, isoleucine or methionine. The acidic glutamate can replace with aspartate etc.... (see Tables 2 and 3 above).

Example 9

Biodistribution of Labeled Mimetope In Vivo

The in vivo targeting potential of [111]-Indium-labeled mimetope was assessed by scintigraphy in an in vivo mouse model of prostate cancer.

Labeling of Mimetope

In order to label the mimetope with [111]-Indium, the peptide was conjugated with the cation chelator 1,4,7,10-tetraazacyclododecane-1,4,7,10-tetraacetic acid (DOTA). The sequence of mimetope (SEQ ID NO:24) was prolonged in Nt by the addition of a lysine-glycine spacer arm to facilitate the coupling of DOTA and avoid potential interference with the PSMA binding region of the peptide. DOTA-mono (N-hydroxysuccinimidyl ester) was conjugated to the amino-terminal lysine through an amide bound (BioSynthesis Inc.).

The peptide conjugate (1 mg) was solubilized in 700 ul of ammonium acetate 0.3M, pH 6.5. Complete solubilization of the peptide was achieved by adding a few microliters of 1M sodium hydroxide. The conjugate solution was then mixed with 200 ul of a solution containing 1 mCi of [111]indium in 0.01M HCl. The mixture was incubated at 43° C. for 1 h. The indium-labeled peptide conjugate was recovered from the free indium by gel filtration. A sample of the solution was counted in a gamma counter to determine the specific activity of the labeled peptide.

The quality of the separation of the labeled peptide from the free was evaluated by thin layer chromatography (TLC). A 2 ul sample of the labeled peptide was mixed with 2 ul of DTPA 1% at a pH of 5.5 and spotted on a silical gel impregnated glass fiber sheet (Pall). The TLC was run in a mobile phase consisting of 1% DTPA pH 5.5. Under those conditions, the free indium migrates with the mobile phase and the peptide-associated indium does not migrate. Upon completion of the chromatography, the top and bottom part of the sheet were counted in a gamma counter and the % of indium associated with the peptide calculated.

Prostate Cancer Mouse Model and Scintigraphy

Male nu/nu CD1 mice of 8 to 12 weeks of age were injected sub-cutaneously in the tight with 1 to $5 \times 10^6$ trypsinized LNCaP (right) or PC-3 (left) cells in a volume of 100 ul of PBS containing 50% matrigel (Becton Dickinson). Up to 4 to 6 weeks after the cells injection, the mice were administered, by tail vein injection, a volume of 50 ul of [111]-indium-labeled mimetope at a concentration of 1 mg/ml in PBS at a specific activity of 0.04 uCi/ug. 3 h and 27 hours post-injection, mice were anesthetized and whole body distribution of [111]-indium labeled peptide measured by scintigraphy over a period of acquisition of 15 minutes.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A peptide consisting of amino acid sequence CysLysGlnSerTyrAsnPheIleThrCys (SEQ ID NO:24) which binds to human prostate specific membrane antigen (PSMA) polypeptide having the amino acid sequence of SEQ ID NO.:2 or a peptide variant thereof having one amino acid among Lys, Gln, Ser, Tyr, Asn or Thr of SEQ ID NO.:24 replaced by a different amino acid, wherein said peptide or peptide variant binds to an extracellular region of PSMA ranging from amino acid 490 to amino acid 500 and wherein said peptide or peptide variant is capable of cyclization.

2. A composition comprising a) the peptide or peptide variant of claim 1, bound to a cytotoxic drug or to a detectable label, and; b) a carrier.

3. The composition according to claim 2, wherein the cytotoxic drug is selected from the group consisting of Iodine-I 31, cyclophosphamide, Yttrium-90, paclitaxel, saporin, Pseudomonas exotoxin (PE40) and/or mixtures thereof.

4. The composition according to claim 2, wherein the detectable label is selected from the group consisting of a radioactive label, a fluorescent label, a nuclear magnetic resonance active label, a luminescent label, a chromophore label, a positron emitting isotope for PET scanner, chemiluminescence label, and an enzymatic label.

5. A peptide consisting of SEQ ID NO: 24.

6. The composition of claim 2, wherein said composition comprises a peptide consisting of SEQ ID NO: 24.

7. The composition of claim 3, wherein said composition comprises a peptide consisting of SEQ ID NO: 24.

8. The composition of claim 4, wherein said composition comprises a peptide consisting of SEQ ID NO: 24.

* * * * *